(12) United States Patent
Green et al.

(10) Patent No.: US 7,601,718 B2
(45) Date of Patent: Oct. 13, 2009

(54) COMPOSITIONS USEFUL AS INHIBITORS OF PROTEIN KINASES

(75) Inventors: Jeremy Green, Waltham, MA (US); Ronald Grey, Attleboro, MA (US); Albert C. Pierce, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 553 days.

(21) Appl. No.: 10/772,219

(22) Filed: Feb. 4, 2004

(65) Prior Publication Data

US 2004/0192682 A1 Sep. 30, 2004

Related U.S. Application Data

(60) Provisional application No. 60/445,529, filed on Feb. 6, 2003.

(51) Int. Cl.
*C07D 487/00* (2006.01)
*A61K 31/50* (2006.01)

(52) U.S. Cl. .................. 514/250; 544/224; 544/235; 544/236

(58) Field of Classification Search ............ 544/224, 544/235, 236; 514/250
See application file for complete search history.

(56) References Cited

U.S. PATENT DOCUMENTS

| | | | |
|---|---|---|---|
| 4,004,009 | A | 1/1977 | Anderson |
| 6,342,601 | B1 | 1/2002 | Bantick et al. |

FOREIGN PATENT DOCUMENTS

| | | |
|---|---|---|
| JP | 2003-82251 | 3/2003 |
| WO | WO 02/22601 | 3/2002 |
| WO | WO 03/080616 | 10/2003 |
| WO | WO 2004/072029 | 8/2004 |

OTHER PUBLICATIONS

Ghozlan et al., "Synthesis of polyfunctionally substited pyridazines", Liebigs Ann. Chem, 1990, 293-296.*
Patel et al., "Synthesis and Biological Activity of Substituted 1,4,5,6-tetrahydropyridazin-4-ones, 5,6-dihydro-3-hydroxy-1*H*-pyrazolo[4,3-c]pyridazines and 2,8-dihydro-1*H*-pyrano[2,3-d]pyridazines", Indian Journal of Chemistry, vol. 28B, pp. 733-744, Sep. 1989.
Ghozlan et al., "Synthesis of Polyfunctionally Substituted Pyridazines", Liebigs Ann. Chem., pp. 293-296, 1990.
Ghozlan et al., "Reactions with 3-oxo-2-phenylhydrazonobutyronitrile: New Routes for the Synthesis of Pyridazines", Gazzetta Chimica Italiana, vol. 119, pp. 95-97, 1989.
Witherington et al., "5-Aryl-pyrazolo[3,4-b]pyridazines: Potent Inhibitors of Glycogen Synthase Kinase-3 (GSK-3)", Bioorganic & Medical Chemistry Letters, vol. 13, pp. 1581-1584, 2003.

* cited by examiner

*Primary Examiner*—James O. Wilson
*Assistant Examiner*—Paul V. Ward
(74) *Attorney, Agent, or Firm*—Jennifer G. Che

(57) ABSTRACT

The present invention provides a compound of formula I:

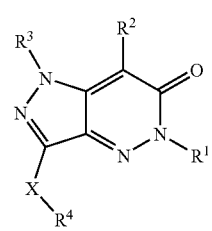

or a pharmaceutically acceptable salt or mixtures thereof. These compounds are inhibitors of protein kinases, particularly inhibitors of GSK mammalian protein kinase, and more particularly inhibitors of GSK-3 mammalian protein kinase. The invention also provides pharmaceutically acceptable compositions comprising the compounds of the invention and methods of utilizing those compounds and compositions in the treatment of various protein kinase mediated disorders.

53 Claims, No Drawings

COMPOSITIONS USEFUL AS INHIBITORS OF PROTEIN KINASES

CROSS REFERENCE TO RELATED APPLICATIONS

The present application claims priority under 35 U.S.C. §119 to U.S. Provisional Application No. 60/445,529, filed Feb. 6, 2003, entitled "Compositions Useful as Inhibitors of Protein Kinases, the entire contents of which is hereby incorporated by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g., osmotic shock, heat shock, ultraviolet radiation, bacterial endotoxin, and H2O2), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

Glycogen synthase kinase-3 (GSK-3) is a serine/threonine protein kinase comprised of α and β isoforms that are each encoded by distinct genes [Coghlan et al., *Chemistry & Biology*, 7, 793-803 (2000); Kim and Kimmel, *Curr. Opinion Genetics Dev.*, 10, 508-514 (2000)]. GSK-3 has been implicated in various diseases including diabetes, Alzheimer's disease, CNS disorders such as manic depressive disorder and neurodegenerative diseases, and cardiomyocyte hypertrophy [see, e.g., WO 99/65897; WO 00/38675; Kaytor and Orr, *Curr. Opin. Neurobiol.*, 12, 275-8 (2000); Haq et al., *J. Cell Biol.*, 151, 117-30 (2000); Eldar-Finkelman, *Trends Mol. Med.*, 8, 126-32 (2002)]. These diseases are associated with the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor β-catenin, the translation initiation factor e1F-2B, as well as ATP citrate lyase, axin, heat shock factor-1, c-Jun, c-myc, c-myb, CREB, and CEPBα. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. GSK-3 is a negative regulator of the insulin-induced signal in this pathway. Normally, the presence of insulin causes inhibition of GSK-3-mediated phosphorylation and deactivation of glycogen synthase. The inhibition of GSK-3 leads to increased glycogen synthesis and glucose uptake [Klein et al., *PNAS*, 93, 8455-9 (1996); Cross et al., *Biochem. J.*, 303, 21-26 (1994); Cohen, *Biochem. Soc. Trans.*, 21, 555-567 (1993); and Massillon et al., *Biochem J.* 299, 123-128 (1994); Cohen and Frame, *Nat. Rev. Mol. Cell. Biol.*, 2, 769-76 (2001)]. However, where the insulin response is impaired in a diabetic patient, glycogen synthesis and glucose uptake fail to increase despite the presence of relatively high blood levels of insulin. This leads to abnormally high blood levels of glucose with acute and chronic effects that may ultimately result in cardiovascular disease, renal failure and blindness. In such patients, the normal insulin-induced inhibition of GSK-3 fails to occur. It has also been reported that GSK-3 is overexpressed in patients with type II diabetes [WO 00/38675]. Therapeutic inhibitors of GSK-3 are therefore useful for treating diabetic patients suffering from an impaired response to insulin.

Apoptosis has been implicated in the pathophysiology of ischemic brain damage (Li et al., 1997; Choi, et al., 1996; Charriaut-Marlangue et al., 1998; Grahm and Chen, 2001; Murphy et al., 1999; Nicotera et al., 1999). Recent publications indicate that activation of GSK-3β may be involved in apoptotic mechanisms (Kaytor and Orr, 2002; Culbert et al., 2001). Studies in rat models of ischemic stroke induced by middle cerebral artery occlusion (MCAO) showed increased GSK-3β expression is following ischemia (Wang et al., *Brain Res.*, 859, 381-5 (2000); Sasaki et al., *Neurol Res.*, 23, 588-92 (2001)). Fibroblast growth factor (FGF) reduced ischemic brain injury after permanent middle cerebral artery occlusion (MCO) in rats (Fisher et al. 1995; Song et al. 2002). Indeed, the neuroprotective effects of FGF demonstrated in ischemia models in rats may be mediated by a PI-3 kinase/AKT-dependent inactivation of GSK-3β (Hashimoto et al., 2002). Thus, inhibition of GSK-3β after a cerebral ischemic event may ameliorate ischemic brain damage.

GSK-3 is also implicated in mycardial infarction. See Jonassen et al., *Circ Res.*, 89, 1191 (2001) (The reduction in myocardial infarction by insulin administration at reperfusion is mediated via Akt dependent signaling pathway.); Matsui et al., *Circulation*, 104, 330 (2001) (Akt activation preserves cardiac function and prevents cardiomyocyte injury after transient cardiac ischemia in vivo); Miao et al., *J. Mol. Cell. Cardiol.*, 32, 2397 (2000) (Intracoronary, adenovirus-mediated Akt gene delivery in heart reduced gross infarct size following ischemia-reperfusion injury in vivo); and Fujio et al., *Circulation*, 101, 660 (2000) (Akt signaling inhibits cardiac myocyte apoptosis in vitro and protects against ischemia-reperfusion injury in mouse heart).

GSK-3 activity plays a role in head trauma. See Noshita et al., *Neurobiol. Dis.*, 9, 294 (2002) (Upregulation of Akt/PI3- kinase pathway may be crucial for cell survival after traumatic brain injury) and Dietrich et al., *J. Neurotrauma*, 13, 309 (1996) (Posttraumatic administration of bFGF significantly reduced damaged cortical neurons & total contusion volume in a rat model of traumatic brain injury).

GSK-3 is also known to play a role in psychiatric disorders. See Eldar-Finkelman, *Trends Mol. Med.*, 8, 126 (2002); Li et al., *Bipolar Disord.*, 4, 137 (2002) (LiCl and Valproic acid, anti-psychotic, mood stabilizing drugs, decrease GSK-3 activities and increase beta-catenin) and Lijam et al., *Cell*, 90, 895 (1997) (Dishevelled KO mice showed abnormal social behavior and defective sensorimotor gating. Dishevelled, a cytoplamic protein involved in WNT pathway, inhibits GSK-3beta activities).

It has been shown that GSK-3 inhibition by lithium and valproic acid induces axonal remodeling and change synaptic connectivity. See Kaytor & Orr, *Curr. Opin. Neurobiol.*, 12, 275 (2002) (Downregulation of GSK-3 causes changes in microtubule-associated proteins: tau, MAP1 & 2) and Hall et al., *Mol. Cell. Neurosci.*, 20, 257 (2002) (Lithium and valproic acid induces the formation of growth cone-like structures along the axons).

GSK-3 activity is also associated with Alzheimer's disease. This disease is characterized by the presence of the well-known β-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Curr. Biol.*, 4, 1077-86 (1994); and Brownlees et al., *Neuroreport*, 8, 3251-55 (1997); Kaytor and Orr, *Curr. Opin. Neurobiol.*, 12, 275-8 (2000)]. In transgenic mice overexpressing GSK-3, a significant increase in Tau hyperphosphorylation and abnormal morphology of neurons was observed [Lucas et al., *EMBO J.*, 20, 27-39 (2001)]. Active GSK-3 accumulates in cytoplasm of pretangled neurons, which can lead to neurofibrillary tangles in brains of patients with AD [Pei et al., *J. Neuropathol. Exp. Neurol.*, 58, 1010-19 (1999)]. Therefore, inhibition of GSK-3 slows or halts the generation of neurofibrillary tangles and thus can treat or reduce the severity of Alzheimer's disease.

Evidence for the role GSK-3 plays in Alzheimer's disease has been shown in vitro. See Aplin et al., *J. Neurochem.* 67, 699 (1996); Sun et al., *Neurosci. Lett.* 321, 61 (2002) (GSK-3b phosphorylates cytoplasmic domain of Amyloid Precursor Protein (APP) and GSK-3b inhibition reduces Ab40 & Ab42 secretion in APP-transfected cells); Takashima et al., *PNAS*, 95, 9637 (1998); Kirschenbaum et al. (2001), *J. Biol. Chem.*, 276, 7366 (2001) (GSK-3b complexes with and phosphorylates presenilin-1, which is associated with gamma-secretase activity in the synthesis of Aβ from APP); Takashima et al., (1998), *Neurosci. Res.* 31, 317 (1998) (Activation of GSK-3b by Ab(25-35) enhances phosphorylation of tau in hippocampal neurons. This observation provides a link between Aβ and neurofibrillary tangles composed of hyperphosphorylated tau, another pathological hallmark of AD); Takashima et al., *PNAS*, 90, 7789 (1993) (Blockade of GSK-3b expression or activity prevents Ab-induced neuro-degeneration of cortical and hippocampal primary cultures); Suhara et al., *Neurobiol. Aging*, 24, 437 (2003) (Intracellular Ab42 is toxic to endothelial cells by interfering with activation of the Akt/GSK-3b signaling-dependent mechanism); De Ferrari et al., *Mol. Psychiatry*, 8, 195 (2003) (Lithium protects N2A cells & primary hippocampal neurons from Aβ fibril-induced cytotoxicity, & reduces nuclear translocation/destabilization of b-catenin); and Pigino et al., *J. Neurosci.*, 23, 4499 (2003) (The mutations in Alzheimer's presenilin 1 may deregulate and increase GSK-3 activity, which in turn, impairs axonal transport in neurons. The consequent reductions in axonal transport in affected neurons can ultimately lead to neurodegeneration).

Evidence for the role GSK-3 plays in Alzheimer's disease has been shown in vivo. See Yamaguchi et al., (1996), *Acta Neuropathol.*, 92, 232 (1996); Pei et al., *J. Neuropath. Exp. Neurol.* 58, 1010 (1999) (GSK-3b immunoreactivity is elevated in susceptible regions of AD brains); Hernandez et al., *J. Neurochem.*, 83, 1529 (2002) (Transgenic mice with conditional GSK-3b overexpression exhibit cognitive deficits similar to those in transgenic APP mouse models of AD); De Ferrari et al., *Mol. Psychiatry*, 8, 195 (2003) (Chronic lithium treatment rescued neurodegeneration and behavioral impairments (Morris water maze) caused by intrahippocampal injection of Aβ fibrils.); McLaurin et al., *Nature Med.*, 8, 1263 (2002) (Immunization with Aβ in a transgenic model of AD reduces both AD-like neuropathology and the spatial memory impairments); and Phiel et al., *Nature*, 423, 435 (2003) (GSK-3 regulates amyloid-beta peptide production via direct inhibition of gamma secretase in AD tg mice).

Presenilin-1 and kinesin-1 are also substrates for GSK-3 and relate to another mechanism for the role GSK-3 plays in Alzheimer's disease, as was recently described by Pigino, G., et al., *Journal of Neuroscience*, 23, 4499 (2003). It was found that GSK-3beta phosphorylates kinsesin-I light chain, which results in a release of kinesin-1 from membrane-bound organelles, leading to a reduction in fast anterograde axonal transport (Morfini et al., 2002). The authors suggest that the mutations in PS1 may deregulate and increase GSK-3 activity, which in turn, impairs axonal transport in neurons. The consequent reductions in axonal transport in affected neurons ultimately leads to neurodegeneration.

GSK-3 is also associated with amyotrophic lateral sclerosis (ALS). See Williamson and Cleveland, 1999 (Axonal transport is retarded in a very early phase of ALS in mSOD1 mice); Morfini et al., 2002 (GSK3 phosphorylates kinesin light chains and inhibit anterograde axonal transport); Warita et al., *Apoptosis*, 6, 345 (2001) (The majority of spinal motor neurons lost the immunoreactivities for both P13-K and Akt in the early and presymptomatic stage that preceded significant loss of the neurons in this SOD1 tg animal model of ALS); and Sanchez et al., 2001 (The inhibition of PI-3K induces neurite retraction mediated by GSK-3 activation).

GSK-3 activity is also linked to spinal cord and peripheral nerve injuries. It has been shown that GSK-3 inhibition by lithium and valproic acid can induce axonal remodeling and change synaptic connectivity. See Kaytor & Orr, *Curr. Opin. Neurobiol.*, 12, 275 (2002) (Downregulation of GSK-3 causes changes in microtubule-associated proteins: tau, MAPI & 2) and Hall et al., *Mol. Cell. Neurosci.*, 20, 257 (2002) (Lithium and valproic acid induces the formation of growth cone-like structures along the axons). See also Grothe et al., *Brain Res.*, 885, 172 (2000) (FGF-2 stimulates Schwann cell proliferation and inhibits myelination during axonal growth); Grothe and Nikkhah, 2001 (FGF-2 is up regulated in the proximal and distal nerve stumps within 5 hours after nerve crush); and Sanchez et al., 2001 (The inhibition of PI-3K induces neurite retraction mediated by GSK-3 activation).

Another substrate of GSK-3 is β-catenin, which is degraded after phosphorylation by GSK-3. Reduced levels of β-catenin have been reported in schizophrenic patients and have also been associated with other diseases related to increase in neuronal cell death [Zhong et al., *Nature*, 395, 698-702 (1998); Takashima et al., *PNAS*, 90, 7789-93 (1993);

Pei et al., *J. Neuropathol. Exp.*, 56, 70-78 (1997); and Smith et al., *Bioorg. Med. Chem.* 11, 635-639 (2001)]. Furthermore, β-catenin and Tcf-4 play a dual role in vascular remodeling by inhibiting vascular smooth muscle cell apoptosis and promoting proliferation (Wang et al., *Circ. Res.*, 90, 340 (2002). Accordingly, GSK-3 is associated with angiogenic disorders. See also Liu et al., *FASEB J.*, 16, 950 (2002) (Activation of GSK-3 reduces hepatocyte growth factor, leading to altered endothelial cell barrier finction and diminished vascular integrity.) and Kim et al., *J. Biol. Chem.*, 277, 41888 (2002) (GSK-3beta activation inhibits angiogenesis in vivo using a Matrigel plug assay: the inhibition of GSK-3beta signalling enhances capillary formation).

Association between GSK-3 and Huntington's disease has been shown. See Carmichael et al., *J. Biol. Chem.*, 277, 33791 (2002) (GSK-3beta inhibition protect cells from polyglutamine-induced neuronal and non-neuronal cell death via increases in b-catenin and its associated transcriptional pathway). Overexpression of GSK-3 reduced the activation of heat shock transcription factor-1 and heat shock protein HSP70 (Bijur et al., *J. Biol. Chem.*, 275, 7583 (2000) that are shown to decrease both poly-(Q) aggregates and cell death in vitro HD model (Wyttenbach et al., *Hum. Mol. Genet.*, 11, 1137 (2002)).

GSK-3 effects the levels of FGF-2 and their receptors which are increased during remyelination of brain aggregate cultures in remyelinating rat brains. See Copelman et al., 2000, Messersmith, et al., 2000; and Hinks and Franklin, 2000. It was also found that FGF-2 induces process outgrowth by oligodendrocytes implicating involvement of FGF in remyelination (Oh and Yong, 1996; Gogate et al., 1994) and that FGF-2 gene therapy has shown to improve the recovery of experimental allergic encephalomyelitis (EAE) mice (Ruffini, et al., 2001).

GSK-3 has also been associated with hair growth because Wnt/beta-catenin signaling is shown to play a major role in hair follicle morphogenesis and differentiation (Kishimotot et al., *Genes Dev.*, 14, 1181 (2000); Millar, *J. Invest. Dermatol.*, 118, 216 (2002)). It was found that mice with constituitive overexpression of the inhibitors of Wnt signaling in skin failed to develop hair follicles. Wnt signals are required for the initial development of hair follicles and GSK-3 constituitively regulates Wnt pathways by inhibiting beta-catenin. (Andl et al., *Dev. Cell*, 2, 643 (2002)). A transient Wnt signal provides the crucial initial stimulus for the start of a new hair growth cycle, by activating beta-catenin and TCF-regulated gene transcription in epithelial hair follicle precursors (Van Mater et al., *Genes Dev.*, 17, 1219 (2003)).

Because GSK-3 activity is associated with sperm motility, GSK-3 inhibition is useful as a male contraceptive. It was shown that a decline in sperm GSK-3 activity is associated with sperm motility development in bovine and monkey epididymis. (Vijayaraghavan et al., *Biol. Reprod.*, 54, 709 (1996); Smith et al., *J. Androl.*, 20, 47 (1999)). Furthermore, tyrosine & serine/threonine phosphorylation of GSK-3 is high in motile compared to immotile sperm in bulls (Vijayaraghavan et al., *Biol. Reprod.*, 62, 1647 (2000)). This effect was also demonstrated with human sperm (Luconi et al., *Human Reprod.*, 16, 1931 (2001)).

Considering the lack of currently available treatment options for the majority of the conditions associated with GSK-3 protein kinase, there is still a great need for new therapeutic agents that inhibit this protein target.

SUMMARY OF THE INVENTION

It has now been found that compounds of this invention, and pharmaceutically acceptable compositions thereof, are effective as inhibitors of GSK protein kinase. These compounds have the general formula I:

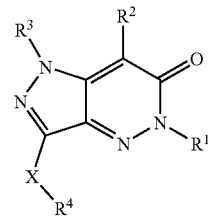

I or a pharmaceutically acceptable salt or mixtures thereof, wherein $R^1$, $R^2$, $R^3$, $R^4$ and X, are as defined below.

The compounds of this invention are capable of inhibiting GSK-3 activity. According to the invention, these compounds are also utilized in compositions and methods for inhibiting GSK-3 activity and methods for treating or lessening the severity of diseases or conditions associated with GSK-3 in patients.

The diseases or conditions amenable to the methods of this invention include, for example, neurological and neurodegenerative disorders, diabetes, psychiatric disorders, multiple sclerosis (MS), myocardial infarction, reperfusion/ischemia, baldness, and stroke.

DETAILED DESCRIPTION OF THE INVENTION

I. General Description of Compounds of the Invention:

The present invention relates to a compound of formula I:

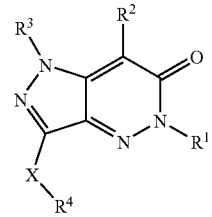

I or a pharmaceutically acceptable salt or mixtures thereof, wherein $R^1$ is selected from $-(L)_m R$, $-(L)_m Ar^1$, or $-(L)_m Cy^1$; L is an optionally substituted $C_{1-6}$ alkylidene chain wherein up to two non-adjacent methylene units of L are optionally replaced by O, NR, NRCO, NRCS, NRCONR, NRCSNR, $NRCO_2$, CO, $CO_2$, CONR, CSNR, OC(O)NR, $SO_2$, $SO_2NR$, $NRSO_2$, $NRSO_2NR$, C(O)C(O), or $C(O)CH_2C(O)$; m is 0 or 1; $Ar^1$ is an optionally substituted aryl group selected from a 3-8 membered monocyclic or an 8-10 membered bicyclic ring having 0-5 heteroatoms independently selected from nitrogen, oxygen, or sulfur; and $Cy^1$ is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur, wherein $Ar^1$ and $Cy^1$ are each independently optionally substituted with up to five substituents selected from $Z-R^Y$; wherein Z is a bond or is a $C_1-C_6$ alkylidene chain wherein up to two non-adjacent methylene units of Z are optionally replaced by CO, $CO_2$, COCO, CONR, CSNR, OCONR, NRNR, NRNRCO, NRCO, NRCS, $NRCO_2$, NRCONR, NRCSNR, SO, $SO_2$, $NRSO_2$, $SO_2NR$, $NRSO_2NR$, O, S, or NR; and each occurrence of $R^Y$ is independently selected from R', halogen, $NO_2$, CN, OR', SR', $N(R')_2$, NR'C(O)R', NR'C(S)R', $NR'C(O)N(R')_2$, $NR'C(S)N(R')_2$, $NR'CO_2R'$, C(O)R', $CO_2R'$, OC(O)R', $C(O)N(R')_2$, $C(S)N(R')_2$, $OC(O)N(R')_2$, SOR', $SO_2R'$, $SO_2N(R')_2$, $NR'SO_2R'$, $NR'SO_2N(R')_2$, C(O)C(O)R', or $C(O)CH_2C(O)R'$;

$R^2$ is selected from halogen, $NO_2$, CN, —SR, —$N(R)_2$, -$(T)_n$R, or -$(T)_n Ar^2$ wherein T is an optionally substituted $C_{1-4}$ alkylidene chain wherein up to two non-adjacent methylene units of T are optionally replaced by O, NR, NRCO, NRCS, NRCONR, NRCSNR, $NRCO_2$, CO, $CO_2$, CONR, CSNR, OC(O)NR, $SO_2$, $SO_2NR$, $NRSO_2$, $NRSO_2NR$, C(O)C(O), or $C(O)CH_2C(O)$; n is 0 or 1; $Ar^2$ is an optionally substituted aryl group selected from a 5-6 membered monocyclic or an 8-10 membered bicyclic ring having 0-5 heteroatoms independently selected from nitrogen, oxygen, or sulfur wherein $Ar^2$ is independently optionally substituted with up to five substituents selected from $Q-R^X$; wherein Q is a bond or is a $C_1-C_6$ alkylidene chain wherein up to two non-adjacent methylene units of Q are optionally replaced by CO, $CO_2$, COCO, CONR, CSNR, OCONR, NRNR, NRNRCO, NRCO, NRCS, $NRCO_2$, NRCONR, NRCSNR, SO, $SO_2$, $NRSO_2$, $SO_2NR$, $NRSO_2NR$, O, S, or NR; and each occurrence of $R^X$ is independently selected from R', halogen, $NO_2$, CN, OR', SR', $N(R')_2$, NR'C(O)R', NR'C(S)R', $NR'C(O)N(R')_2$, $NR'C(S)N(R')_2$, $NR'CO_2R'$, C(O)R', $CO_2R'$, OC(O)R', $C(O)N(R')_2$, $C(S)N(R')_2$, $OC(O)N(R')_2$, SOR', $SO_2R'$, $SO_2N(R')_2$, $NR'SO_2R'$, $NR'SO_2N(R')_2$, C(O)C(O)R', or $C(O)CH_2C(O)R'$;

$R^3$ is hydrogen or an optionally substituted $C_{1-4}$ aliphatic group;

X is selected from a valence bond, O, S, or NR;

$R^4$ is selected from —R, —$(U)_j Ar^3$, or —$(U)_j Cy^3$; U is an optionally substituted $C_{1-6}$ alkylidene chain wherein up to two non-adjacent methylene units of U are optionally replaced by O, NR, NRCO, NRCS, NRCONR, NRCSNR, $NRCO_2$, CO, $CO_2$, CONR, CSNR, OC(O)NR, $SO_2$, $SO_2NR$, $NRSO_2$, $NRSO_2NR$, C(O)C(O), or $C(O)CH_2C(O)$; j is 0 or 1; $Ar^3$ is an optionally substituted aryl group selected from a 3-8 membered monocyclic or an 8-10 membered bicyclic ring having 0-5 heteroatoms independently selected from nitrogen, oxygen, or sulfur; and $Cy^3$ is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur, wherein $Ar^3$ and $Cy^3$ are each independently optionally substituted with up to five substituents selected from $Y-R^Z$; wherein Y is a bond or is a $C_1-C_6$ alkylidene chain wherein up to two non-adjacent methylene units of Y are optionally replaced by CO, $CO_2$, COCO, CONR, CSNR, OCONR, NRNR, NRNRCO, NRCO, NRCS, $NRCO_2$, NRCONR, NRCSNR, SO, $SO_2$, $NRSO_2$, $SO_2NR$, $NRSO_2NR$, O, S, or NR; and each occurrence of $R^Z$ is independently selected from R', halogen, $NO_2$, CN, OR', SR', $N(R')_2$, NR'C(O)R', NR'C(S)R', $NR'C(O)N(R')_2$, $NR'C(S)N(R')_2$, $NR'CO_2R'$, C(O)R', $CO_2R'$, OC(O)R', $C(O)N(R')_2$, $C(S)N(R')_2$, $OC(O)N(R')_2$, SOR', $SO_2R'$, $SO_2N(R')_2$, $NR'SO_2R'$, $NR'SO_2N(R')_2$, C(O)C(O)R', or $C(O)CH_2C(O)R'$; or wherein $R^4$ and R, taken together with the nitrogen form an optionally substituted 5-8 membered heterocyclyl or heteroaryl ring having 1-3 heteroatoms independently selected from nitrogen, oxygen, or sulfur;

each occurrence of R is independently selected from hydrogen or an optionally substituted $C_{1-6}$ aliphatic group, or two R on the same nitrogen are taken together with the nitrogen to form a 5-8 membered heterocyclyl or heteroaryl ring having 1-3 heteroatoms independently selected from nitrogen, oxygen, or sulfur; and each occurrence of R' is independently selected from hydrogen or an optionally substituted group selected from $C_{1-6}$ aliphatic, $C_{6-10}$ aryl, a heteroaryl ring having 5-10 ring atoms, or a heterocyclyl ring having 3-10 ring atoms, or wherein two R on the same nitrogen are taken together with the nitrogen to form a 5-8 membered heterocyclyl or heteroaryl ring having 1-3 heteroatoms independently selected from nitrogen, oxygen, or sulfur.

In certain embodiments, for compounds of formula I one or more, or all of the following conditions apply:

a) when X is NR; R, $R^3$, and $R^4$ are each hydrogen; $R^2$ is -$(T)_n$R wherein n is zero and R is hydrogen; and $R^1$ is -$(L)_m Ar^1$ wherein m is 0; then $Ar^1$ is not:
  i) 4-Cl or 4-OMe phenyl; or
  ii) 3-$CF_3$ phenyl;

b) when X is NR; R and $R^3$ are each hydrogen; $R^2$ is -$(T)_n$R wherein n is 0 and R is hydrogen; $R^4$ is 2-phenyl-4-quinazolinyl; and $R^1$ is -$(L)_m Ar^1$ wherein m is 0; then $Ar^1$ is not:
  i) phenyl, 3-OMe phenyl, 4-OMe phenyl, 2,4-diCl phenyl, 4-Cl phenyl, 3-$CF_3$ phenyl, or 4-OPh phenyl;

c) when X is NR; R and $R^3$ are each hydrogen; $R^2$ is -$(T)_n$R wherein n is 0 and R is hydrogen; $R^4$ is 2-(2-trifluoromethyl-phenyl)-4-quinazolinyl; and $R^1$ is -$(L)_m Ar^1$ wherein m is 0; then $Ar^1$ is not phenyl.

d) when X is a valence bond; $R^4$ is hydrogen; $R^3$ is $CH_3$; $R^2$ is either chloro or hydrogen; and $R^1$ is -$(L)_m Ar^1$ wherein m is 0, then $Ar^1$ is not 3-trifluoromethyl phenyl or 2-fluoro-5-trifluoromethyl phenyl.

e) when X is a valence bond; $R^4$ is methyl; $R^3$ is hydrogen; and $R^2$ is cyano, then $R^1$ is not phenyl.

f) when X is a valence bond; $R^4$ is methyl; $R^2$ is -$(T)_n$R wherein n is 0 and R is hydrogen; $R^3$ is hydrogen; and $R^1$ is -$(L)_m Ar^1$ wherein m is 0; then $Ar^1$ is not 4-tolyl.

g) when X is a valence bond; $R^4$ is methyl; $R^3$ is hydrogen; and $R^1$ is -$(L)_m Ar^1$ wherein m is 0; and $Ar^1$ is substituted phenyl; then $R^2$ is not 4-nitrophenoxy.

h) when X is a valence bond; $R^3$ is hydrogen; $R^2$ is -$(T)_n$R wherein n is 0 and R is hydrogen; $R^1$ is -$(L)_m Ar^1$ wherein m is 0; and $Ar^1$ is 2-pyridyl or 4-Cl phenyl; then $R^4$ is not phenyl with an amide in the para position.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The terms "alkyl", "alkenyl" and "alkynyl" used alone or as part of a larger moiety shall include both straight and branched chains containing one to four carbon atoms and at least two carbon atoms and one double bond in the case of alkenyl and at least two carbon atoms and one triple bond, in the case of alkynyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S) R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N (R°)$_2$; —OC(O)N(R°)$_2$; —OC(O)R°; —C(O)N(OR°) R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$NHC(O)R° wherein each independent occurrence of R° is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of R° are selected from $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2H$, $CO_2$($C_{1-4}$aliphatic), O(halo$C_{1-4}$ aliphatic), or halo$C_{1-4}$aliphatic, wherein each of the foregoing $C_{1-4}$aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from —$R^+$, —N($R^+$)$_2$, —C(O)$R^+$, —$CO_2R^+$, —C(O)C(O)$R^+$, —C(O)$CH_2$C(O)$R^+$, —$SO_2R^+$, —$SO_2$N($R^+$)$_2$, —C(=S)N($R^+$)$_2$, —C(=NH)—N($R^+$)$_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —($CH_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of $R^+$ are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or $R^+$, or any other variable similarly defined herein), are taken together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R° (or $R^+$, or any other variable similarly defined herein) are taken together with the atom(s) to which each variable is bound include, but are not limited to the following: a) two independent occurrences of R° (or $R^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or $R^+$, or any other variable similarly defined herein) that are bound to different atoms and are taken together with both of those atoms to form a ring, for example where a phenyl group is substituted with two occurrences of OR°

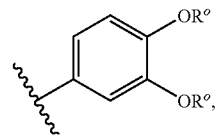

these two occurrences of R° are taken together with the oxygen atoms to which they are bound to form a fused 6-membered oxygen containing ring:

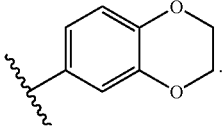

It will be appreciated that a variety of other rings can be formed when two independent occurrences of R° (or $R^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention.

II. Embodiments:

As described generally above, in certain embodiments, $R^1$ is -(L)$_m$Ar$^1$, -(L)$_m$R, or -(L)$_m$Cy$^1$. In another embodiment, $R^1$ is -(L)$_m$Ar$^1$ and compounds have the general formula IA:

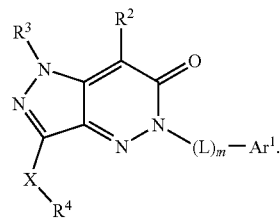

IA

In another embodiment, where $R^1$ is $-(L)_m Ar^1$, $Ar^1$ is selected from one of the following groups:
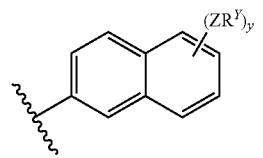
1-1
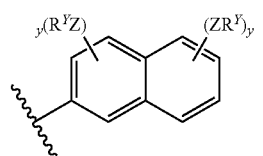
1-2
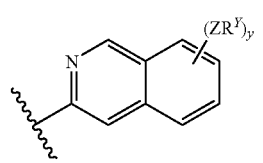
1-3
1-4
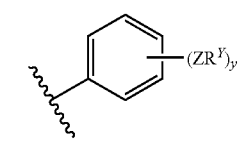
1-5
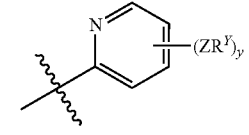
1-6
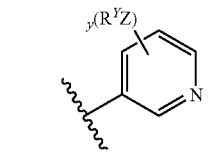
1-7
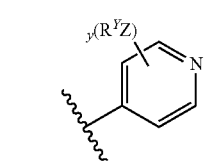
1-8
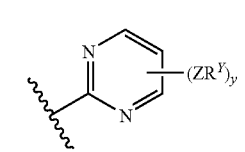
1-9
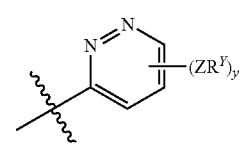
1-10
-continued
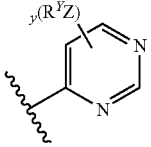
1-11
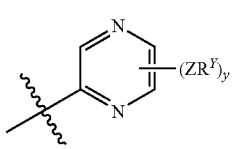
1-12
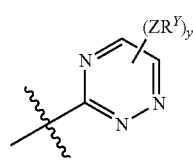
1-13
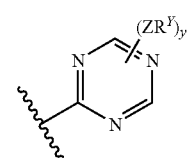
1-14
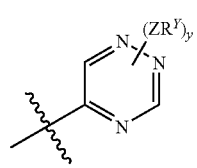
1-15
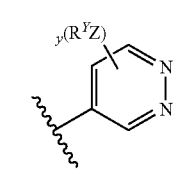
1-16
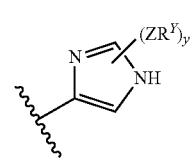
1-17
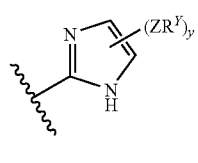
1-18
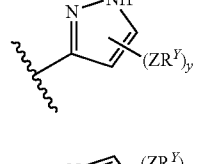
1-19
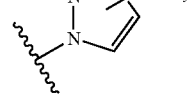
1-20

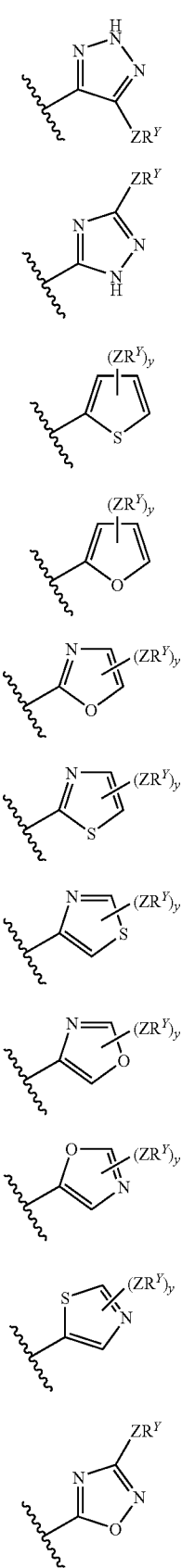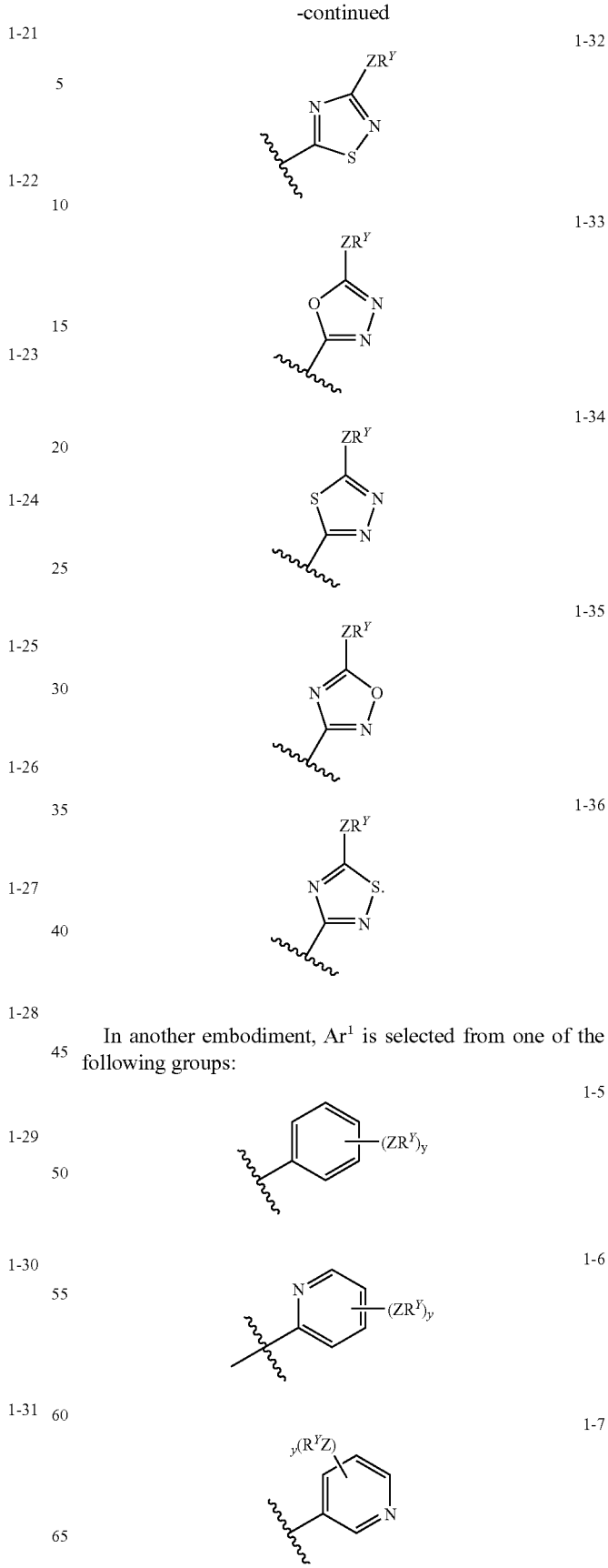
In another embodiment, Ar¹ is selected from one of the following groups:

-continued
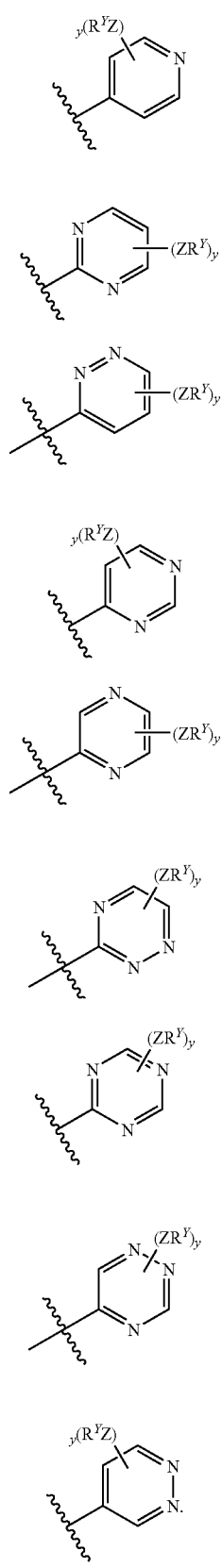
In another embodiment, Ar$^1$ is selected from one of the following groups:
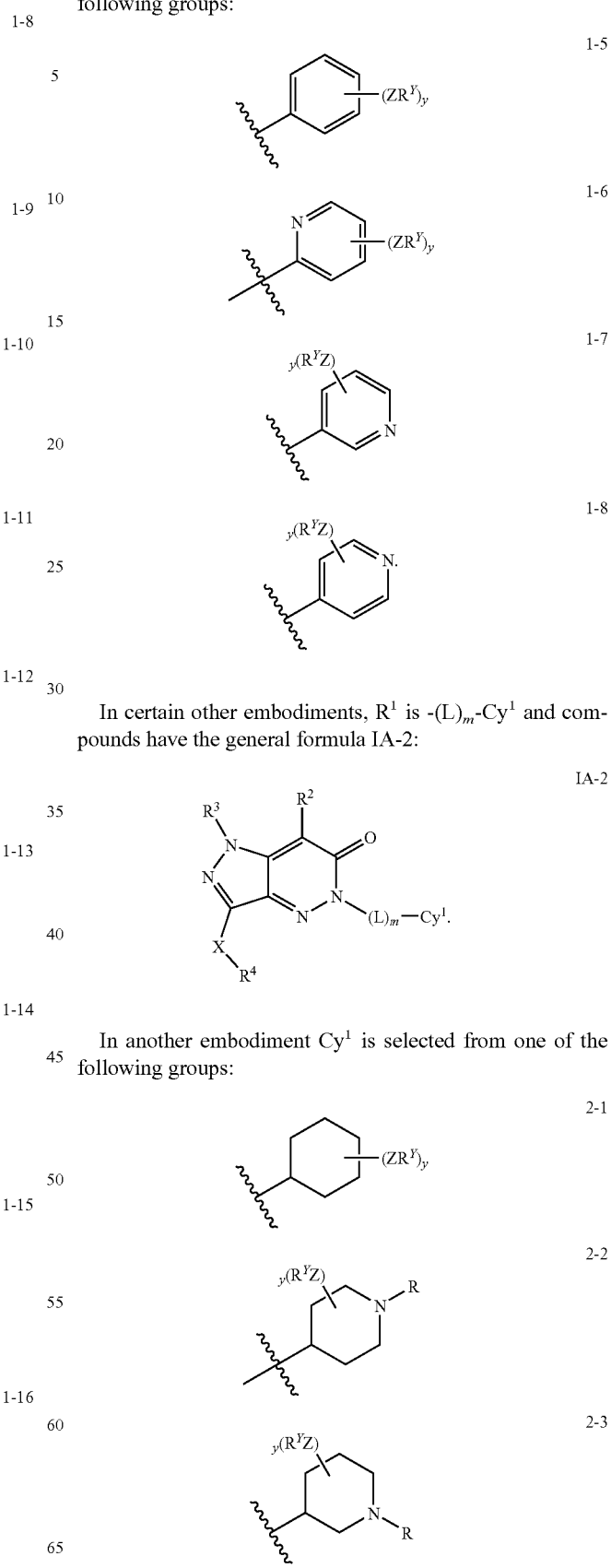
In certain other embodiments, R$^1$ is -(L)$_m$-Cy$^1$ and compounds have the general formula IA-2:
IA-2
In another embodiment Cy$^1$ is selected from one of the following groups:

-continued

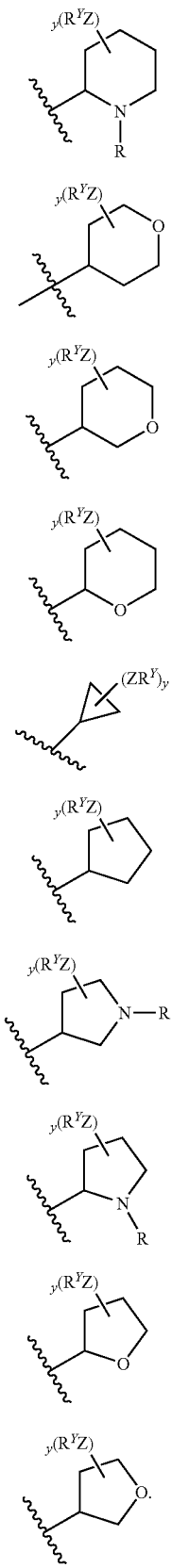

In another embodiment, $R^1$ is $-(L)_m-Ar^1$, m is 1 and compounds have the formula IA-3:

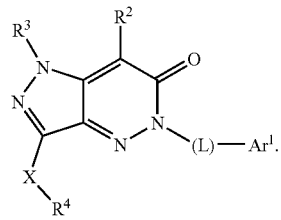

IA-3

In another embodiment $Ar^1$ is phenyl substituted with 0-3 occurrences of $ZR^Y$ and compounds have the general formula IA-1-5:

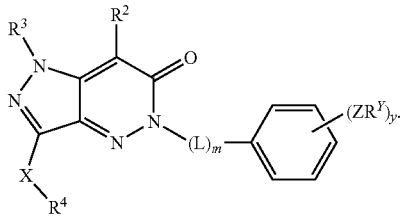

IA-1-5

For each of the subsets described above, L is an optionally substituted $C_{1-6}$ straight or branched alkylidene chain wherein up to 2 non-adjacent methylene units of L are optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O) and m is 1.

In other embodiments, L is an optionally substituted $C_{1-6}$ straight or branched alkylidene chain wherein one methylene unit of L is optionally replaced by CO, CO$_2$, CONR, CSNR, SO$_2$NR, and m is 1.

In yet other embodiments, compounds of formula I and subsets thereof include those compounds wherein $R^1$ is $-(L)_m$R, L is an optionally substituted $C_{1-6}$ straight or branched alkylidene chain wherein one methylene unit of L is optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O), R is an optionally substituted $C_{1-6}$ aliphatic group, and m is 1.

As described generally above, in certain embodiments, $R^2$ is selected from halogen, NO$_2$, CN, —SR, —N(R)$_2$, or -(T)$_n$R, wherein R is selected from hydrogen or an optionally substituted $C_{1-6}$ aliphatic group, or two R on the same nitrogen are taken together with the nitrogen to form a 5-8 membered heterocyclyl or heteroaryl ring having 1-3 heteroatoms independently selected from nitrogen, oxygen, or sulfur.

In another embodiment, $R^2$ is selected from —N(R)$_2$, or -(T)$_n$R, wherein n is 0, and R is selected from hydrogen or an optionally substituted $C_{1-6}$ aliphatic group.

In another embodiment, $R^2$ is -(T)$_n$R, wherein n is 0, and R is selected from hydrogen, CH$_3$, or CF$_3$.

In yet another embodiment, $R^2$ is -(T)$_n$R, wherein n is 0, R is hydrogen, and compounds have the formula IB:

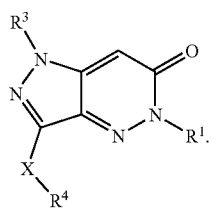

As described generally above, in certain embodiments, $R^3$ is hydrogen, methyl, ethyl, propyl, or isopropyl.

In certain other embodiments, $R^3$ is hydrogen or methyl.

In another embodiment, $R^3$ is hydrogen and compounds have the formula IC:

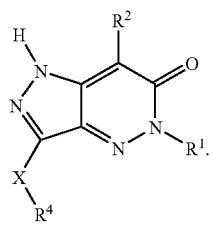

As described generally above, in certain embodiments, X is selected from a valence bond or NR. In certain other embodiments, X is NR and R is hydrogen.

In another embodiment, X is NR, R is hydrogen, and compounds have the formula ID:

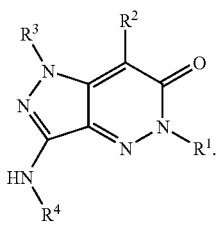

In certain other embodiments, X is $OR^4$ and compounds have the formula IE:

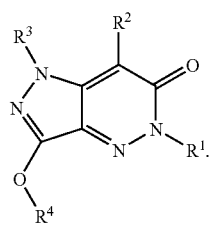

In yet other embodiments, X is $SR^4$ and compounds have the formula IF:

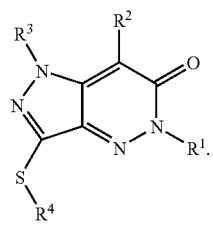

As described generally above, in certain other embodiments, $R^4$ is —(U)$_j$Ar$^3$, —(U)$_j$R, or —(U)$_j$Cy$^3$.

In yet other embodiments, $R^4$ is —(U)$_j$Ar$^3$ and compounds have the general formula IG:

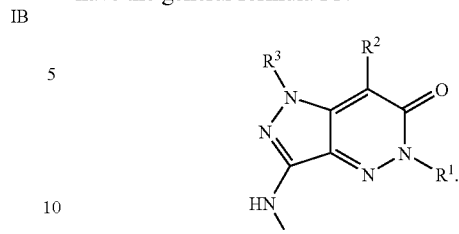

In another embodiment, $R^4$ is —(U)$_j$Ar$^3$, and Ar$^3$ is selected from one of the following groups:

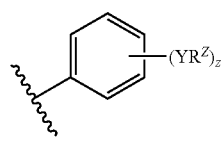

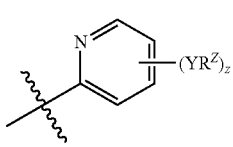

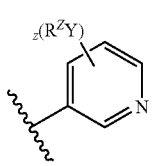

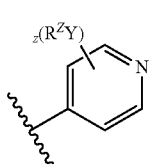

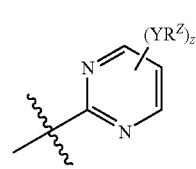

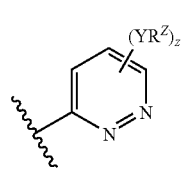

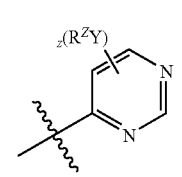

-continued
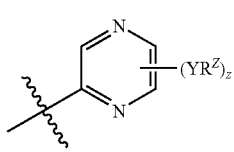
1-12-a
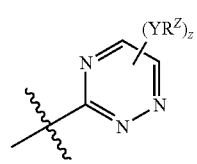
1-13-a
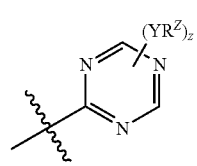
1-14-a
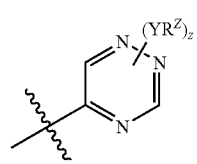
1-15-a
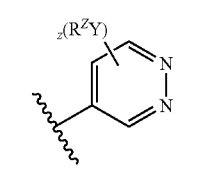
1-16-a
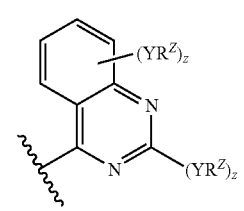
1-37
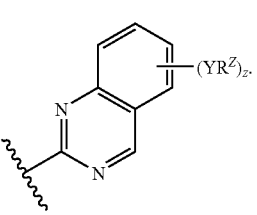
1-38
In other embodiments, Ar³ is selected from one of the following groups:
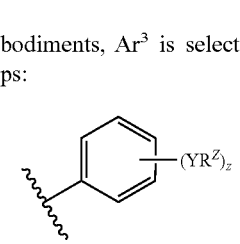
1-5-a
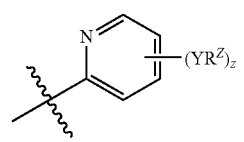
1-6-a
-continued
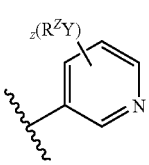
1-7-a
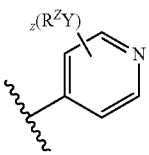
1-8-a
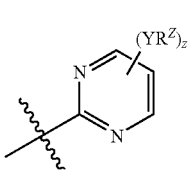
1-9-a
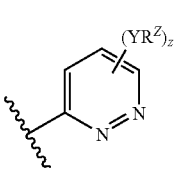
1-10-a
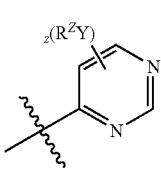
1-11-a
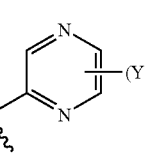
1-12-a
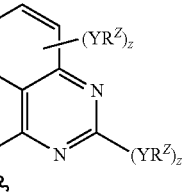
1-37
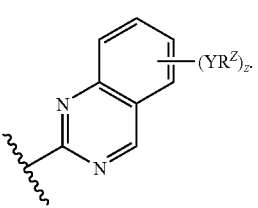
1-38
In other embodiments, Ar³ is selected from one of the following groups:
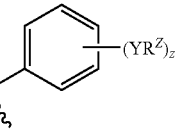
1-5-a -continued
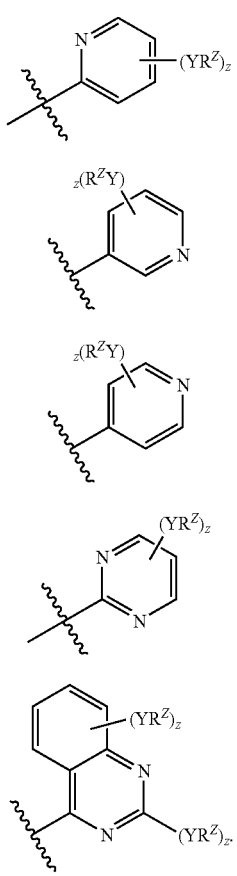
1-6-a
1-7-a
1-8-a
1-9-a
1-37
In another embodiment, $R^4$ is $—(U)_j Ar^3$, and $Ar^3$ is selected from one of the following groups:
IH
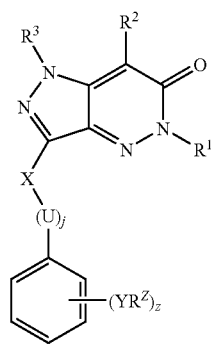
IJ
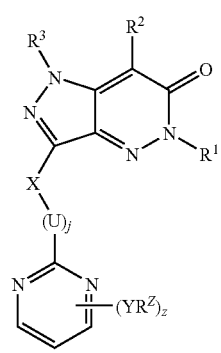
-continued
IK
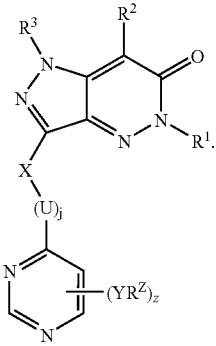
In certain other embodiments, $R^4$ is $—(U)_j Cy^3$ and compounds have the general formula IG-1:
IG-1
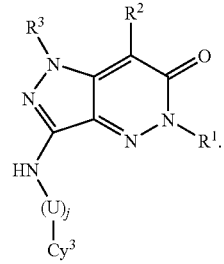
In other embodiments, $Cy^3$ is selected from one of the following groups:
2-1
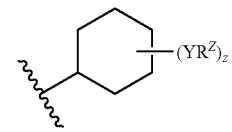
2-2
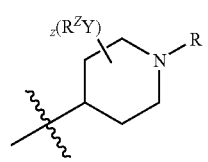
2-3
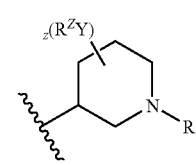
2-4
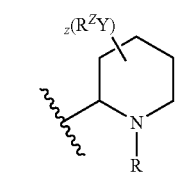
2-5
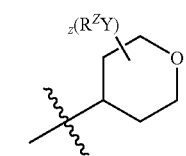

-continued

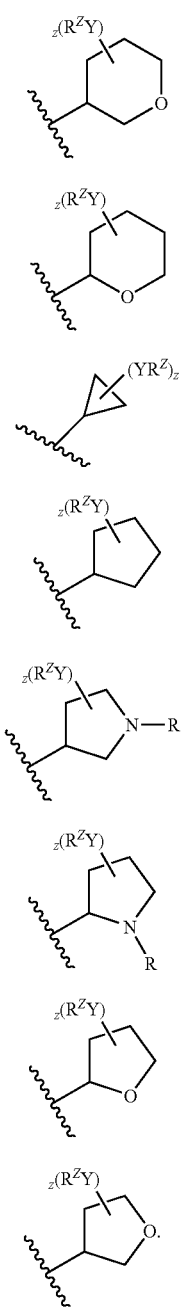

2-6

2-7

2-8

2-9

2-10

2-11

2-12

2-13

In certain other embodiments, X is NR wherein R is hydrogen, R$^4$ is hydrogen, and compounds have the formula IL:

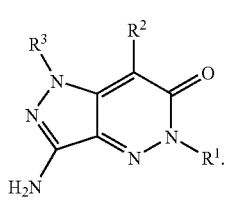

IL

In yet other embodiments, X is a valence bond and compounds have the formula IM:

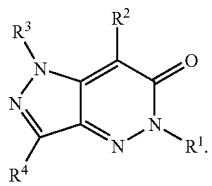

IM

In still other embodiments, R$^4$ is R and R is an optionally substituted C$_{1-6}$ aliphatic group.

As described generally above, in certain embodiments of compounds of formula I, y is 0-5, and Ar$^1$ and Cy$^1$ are independently substituted with 0-5 occurrences of ZR$^Y$. Additionally, Ar$^3$ and Cy$^3$ are independently substituted with 0-5 occurrences of YR$^Z$. In certain other embodiments for compounds of formula I and subsets thereof, each occurrence of ZR$^Y$ and YR$^Z$ is independently halogen, NO$_2$, CN, or an optionally substituted group selected from C$_{1-4}$ aliphatic, aryl, aralkyl, —N(R')$_2$, —CH$_2$N(R')$_2$, —OR', —CH$_2$OR', —SR', —CH$_2$SR', —COOR', or —S(O)$_2$N(R')$_2$. In yet other embodiments, each occurrence of ZR$^Y$ and YR$^Z$ is independently Cl, CF$_3$, NO$_2$, —S(O)$_2$N(R')$_2$ or an optionally substituted group selected from C$_{1-4}$ alkoxy, phenyl, phenyloxy, benzyl, or benzyloxy.

In another embodiment of compounds of formula I, y is 0, and Ar$^1$ is unsubstituted.

In other embodiments, R$^1$ is -(L)$_m$Ar$^1$, m is 0 or 1, Ar$^1$ is phenyl optionally substituted with 0-5 occurrences of ZR$^Y$, and compounds have the formula IIA or IIA-1:

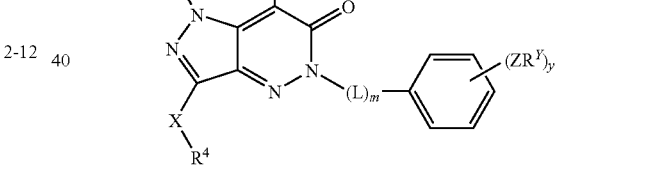

IIA

IIA-1

In certain other embodiments, R$^2$ is -(T)$_n$R, wherein n is 0 and R is hydrogen, R$^1$ is -(L)$_m$Ar$^1$, wherein m is 0 or 1, Ar$^1$ is phenyl optionally substituted with 0-5 occurrences of ZR$^Y$, and compounds have the formula IIB or IIB-1:

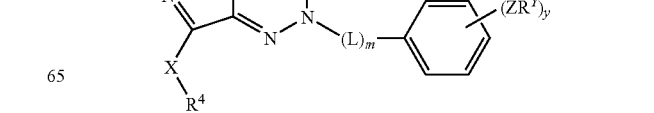

IIB

-continued

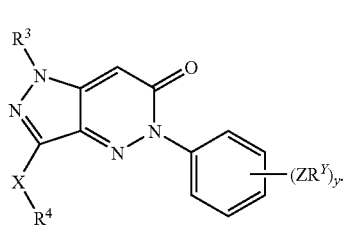
IIB-1

In other embodiments, $R^2$ is $-(T)_nR$, wherein n is 0 and R is hydrogen, $R^3$ is hydrogen, $R^1$ is $-(L)_mAr^1$ wherein m is 0 or 1, $Ar^1$ is phenyl optionally substituted with 0-5 occurrences of $ZR^Y$, and compounds have the formula IIC or IIC-1:

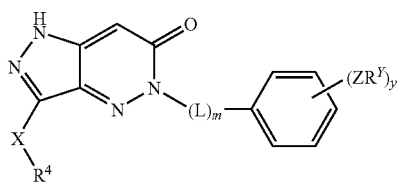
IIC

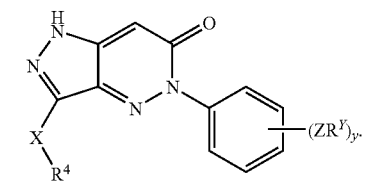
IIC-1

In yet other embodiments, $R^3$ is hydrogen, $R^2$ is $-(T)_nR$, wherein n is 0 and R is hydrogen, X is NR, $R^1$ is $-(L)_mAr^1$ wherein m is 0 or 1, $Ar^1$ is phenyl optionally substituted with 0-5 occurrences of $ZR^Y$, and compounds have the formula IID or IID-1:

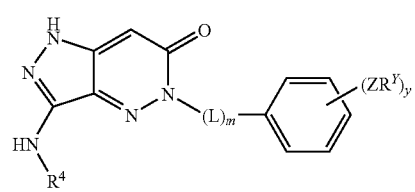
IID

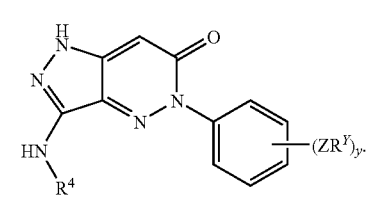
IID-1

In still other embodiments, $R^3$ is hydrogen, $R^2$ is $-(T)_nR$, wherein n is 0 and R is hydrogen, $R^1$ is $-(L)_mAr^1$ wherein m is 0 or 1, $Ar^1$ is phenyl optionally substituted with 0-5 occurrences of $ZR^Y$, and compounds have the formula IIE, IIE-1, IIF, IIF-1, IIG, or IIG-1:

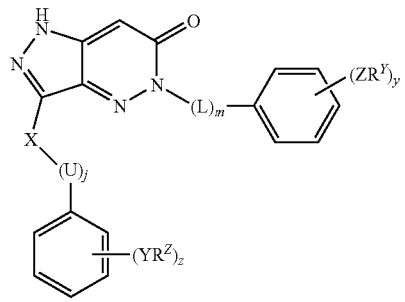
IIE

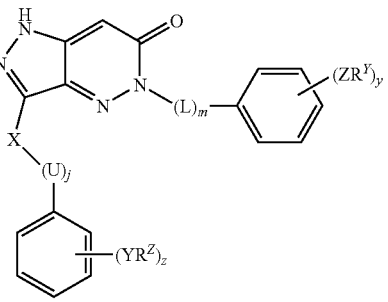
IIE-1

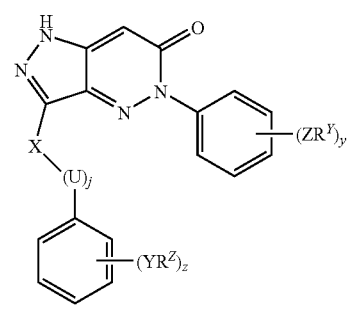
IIF

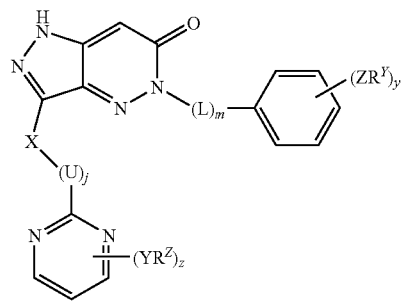
IIF-1

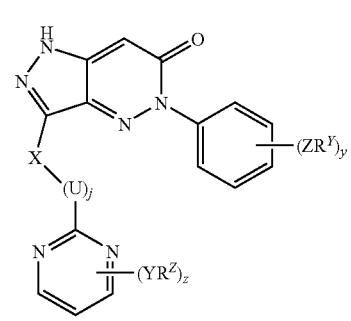
IIG

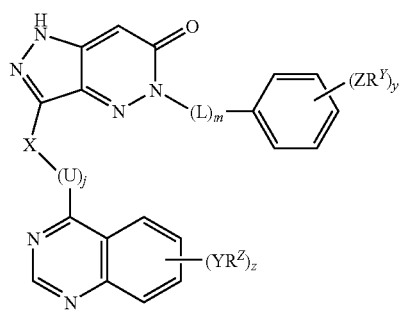

-continued

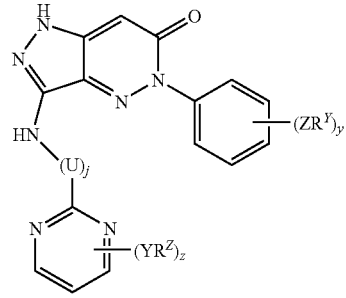
IIG-1

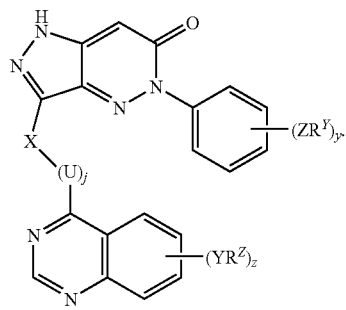
IIIE

In certain other embodiments, R³ is hydrogen, R² is -(T)ₙR, wherein n is 0 and R is hydrogen, X is NH, R¹ is -(L)ₘAr¹ wherein m is 0 or 1, Ar¹ is phenyl optionally substituted with 0-5 occurrences of ZR$^Y$, and compounds have the formula IIIE, IIIE-1, IIIF, IIIF-1, IIIG, or IIIG-1:

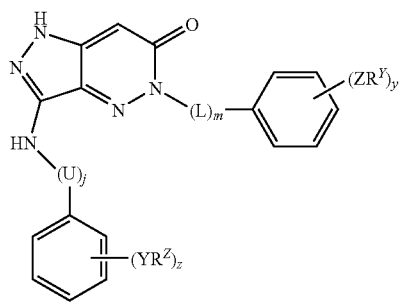
IIIE

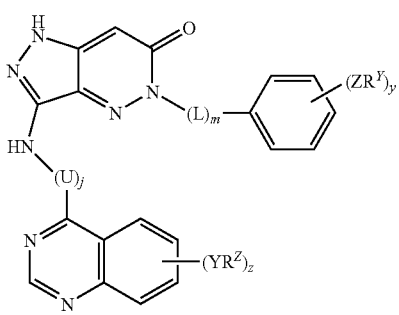
IIIG

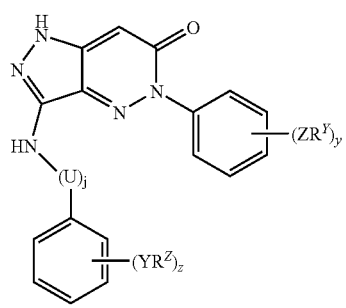
IIIE-1

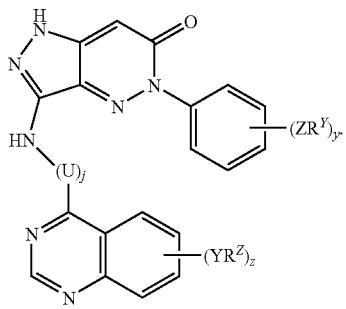
IIIG-1

In still other embodiments, R³ and R⁴ are hydrogen, R² is -(T)ₙR, wherein n is 0 and R is hydrogen, X is NR, Ar¹ is optionally substituted phenyl, R¹ is -(L)ₘAr¹, and compounds have the formula IIH or IIH-1:

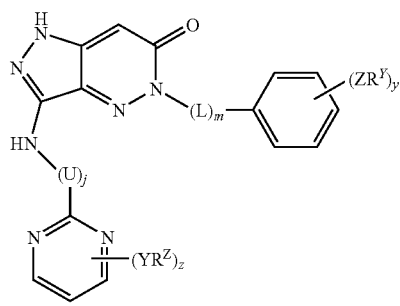
IIIF

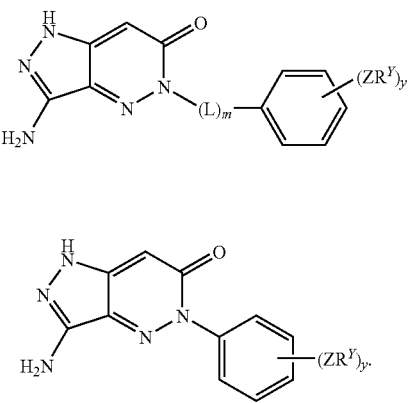
IIH

IIH-1

In other embodiments, $R^3$ and $R^4$ are hydrogen, $R^2$ is $-(T)_n$R, wherein n is 0 and R is hydrogen, X is a valence bond, $Ar^1$ is optionally substituted phenyl, $R^1$ is $-(L)_m Ar^1$, and compounds have the formula IIJ or IIJ-1:

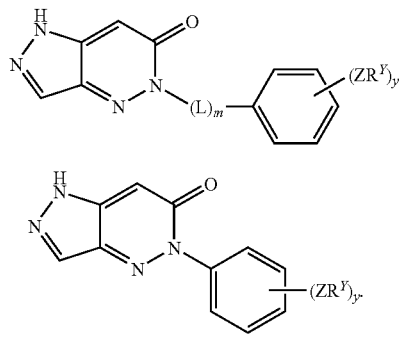

IIJ

IIJ-1

In another embodiment, certain subclasses of the foregoing compounds IIA, IIA-1, IIB, IIB-1, IIC, IIC-1, IID, IID-1, IIE, IIE-1, IIF, IIF-1, IIG, IIG-1, IIH, IIH-1, IIJ, IIJ-1, IIIE, IIIE-1, IIIF, IIIF-1, IIIG, or IIIG-1 are of interest.

For example, in certain embodiments, for compounds described above, $Ar^1$ is phenyl optionally substituted with 0-5 occurrences of $ZR^Y$ or $Ar^1$ is pyridyl optionally substituted with 0-3 occurrences of $ZR^Y$. In other embodiments, m is 0 or m is 1 and L is $CH_2$; y is 0-3; and each occurrence of $ZR^Y$ is independently halogen, $NO_2$, CN, or an optionally substituted group selected from $C_{1-4}$ aliphatic, aryl, aralkyl, $-N(R')_2$, $-CH_2N(R')_2$, $-OR'$, $-CH_2OR'$, $-SR'$, $-CH_2SR'$, $-COOR'$, or $-S(O)_2N(R')_2$. In other embodiments, each occurrence of $ZR^Y$ is independently Cl, $CF_3$, $NO_2$, $-S(O)_2N(R')_2$ or an optionally substituted group selected from $C_{1-4}$ alkoxy, phenyl, phenyloxy, benzyl, or benzyloxy.

For compounds of formula IIA, IIA-1, IIB, IIB-1, IIC, IIC-1, IID, IID-1, IIE, IIE-1, IIF, IIF-1, IIG, IIG-1, IIIE, IIIE-1, IIIF, IIIF-1, IIIG, or IIIG-1, $Ar^3$ is pyridyl or pyrimidinyl each optionally substituted with 0-3 occurrences of $YR^Z$ or phenyl or quinazolyl each optionally substituted with 0-5 occurrences of $YR^Z$. In other embodiments, for compounds described above, j is 0 or j is 1 and U is $CH_2$; X is NH; m is 0 or m is 1 and L is $CH_2$; y is 0-5; and each occurrence of $ZR^Y$ or $YR^Z$ are each independently halogen, $NO_2$, CN, or an optionally substituted group selected from $C_{1-4}$ aliphatic, aryl, aralkyl, $-N(R')_2$, $-CH_2N(R')_2$, $-OR'$, $-CH_2OR'$, $-SR'$, $-CH_2SR'$, $-COOR'$, or $-S(O)_2N(R')_2$.

It is understood that all combinations and subcombinations of embodiments, as described herein, are within the scope of the present invention.

Representative examples of compounds of formula I are set forth below in Table 1.

TABLE 1

Examples of Compounds of Formula I:

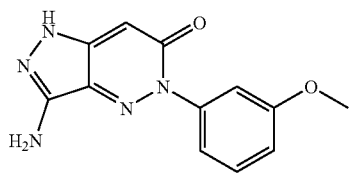

I-1

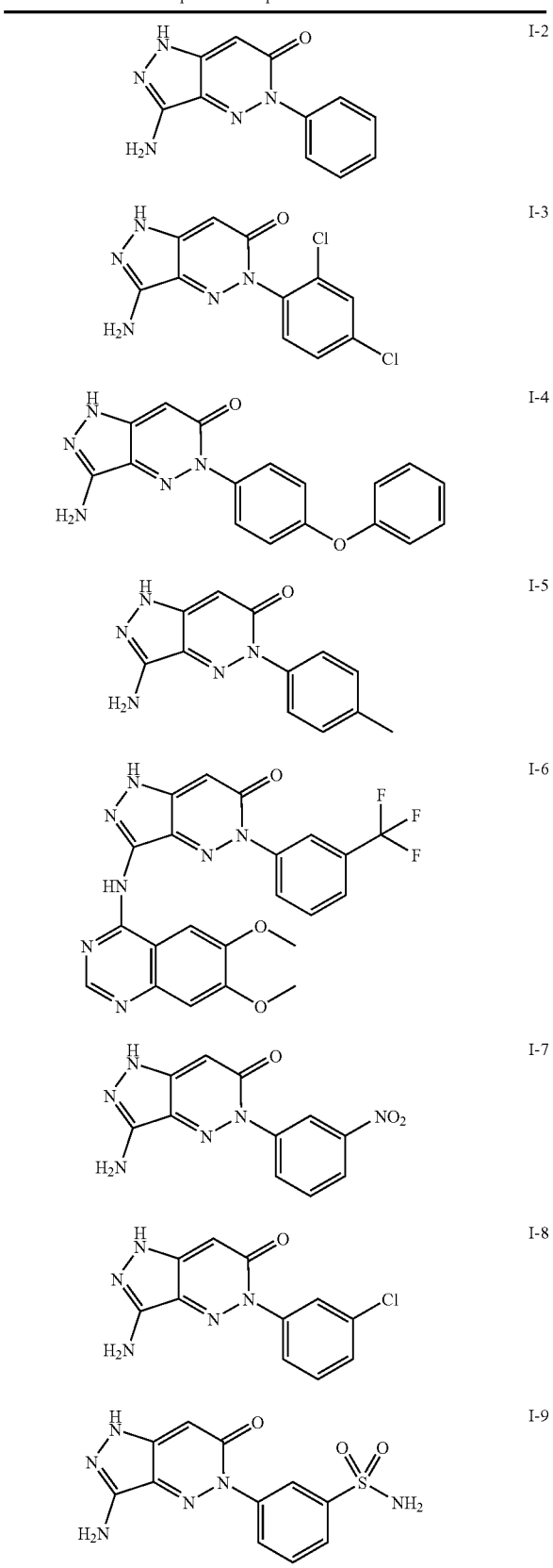

TABLE 1-continued

Examples of Compounds of Formula I:

TABLE 1-continued
Examples of Compounds of Formula I:
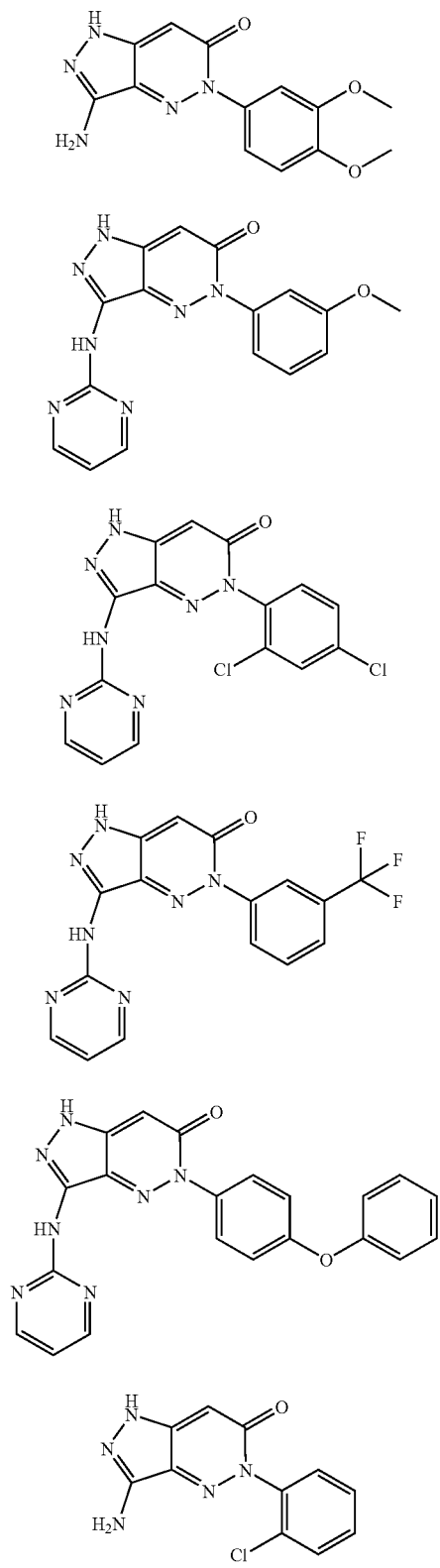
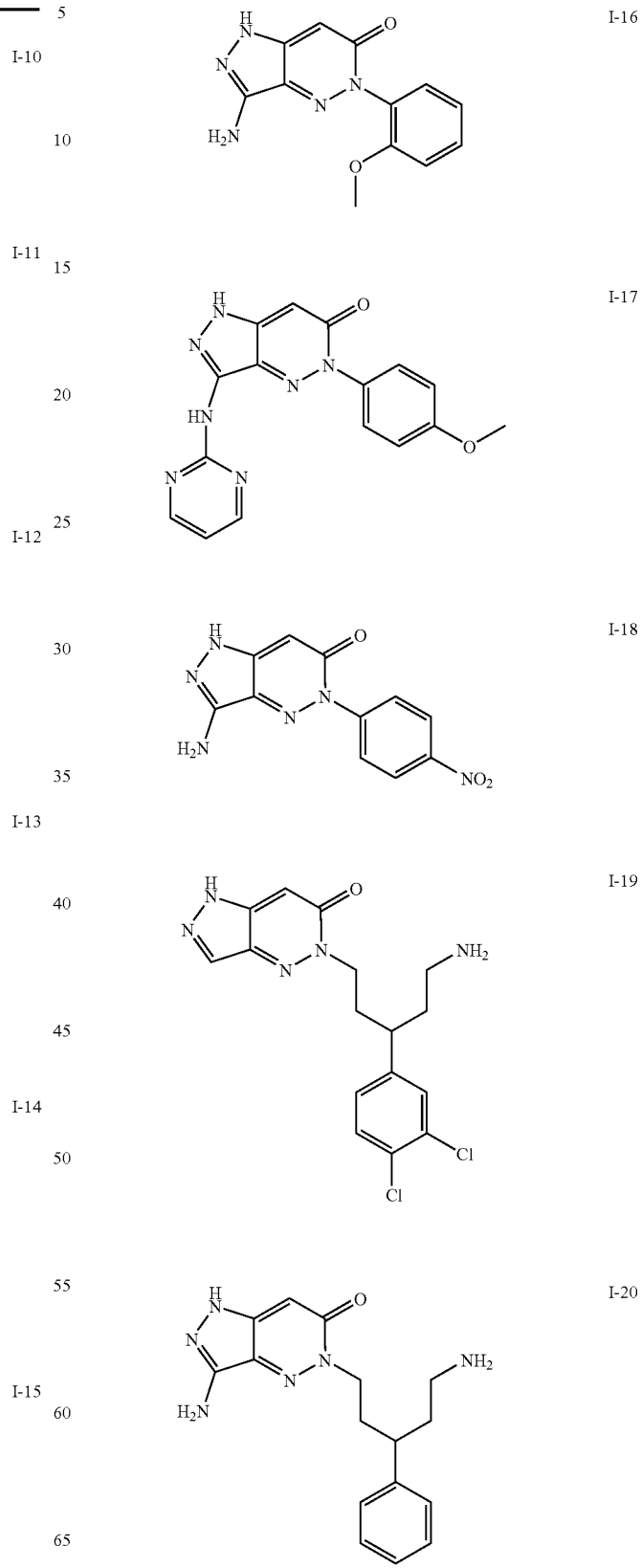

TABLE 1-continued
Examples of Compounds of Formula I:
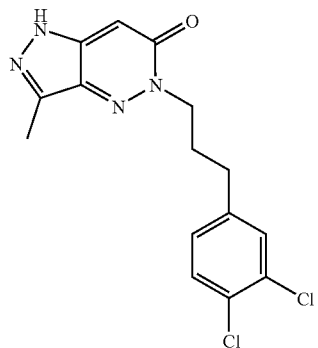 I-21
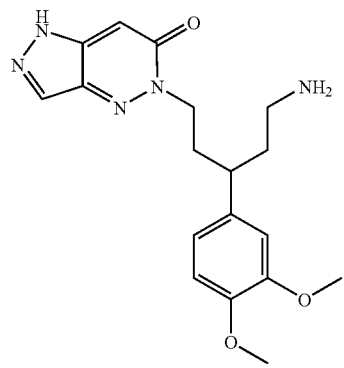 I-22
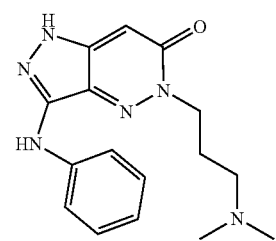 I-23
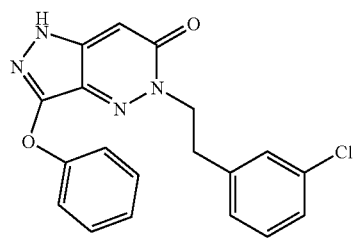 I-24
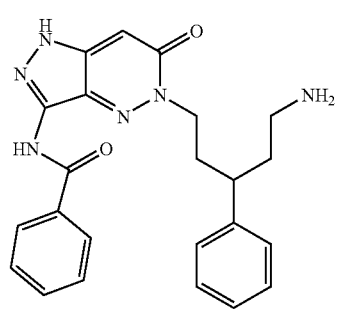 I-25
TABLE 1-continued
Examples of Compounds of Formula I:
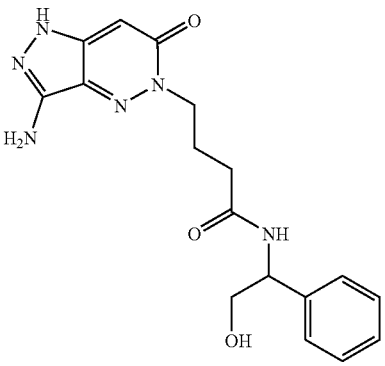 I-26
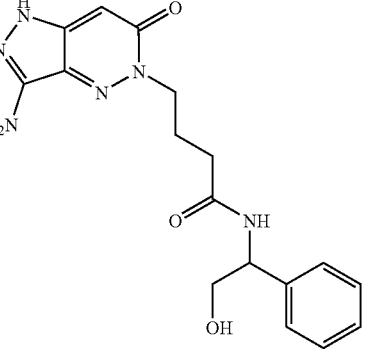 I-27
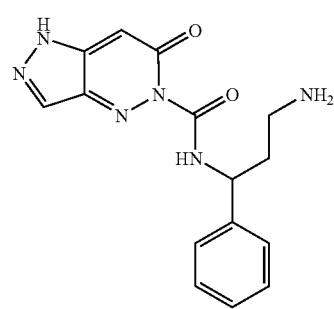 I-28
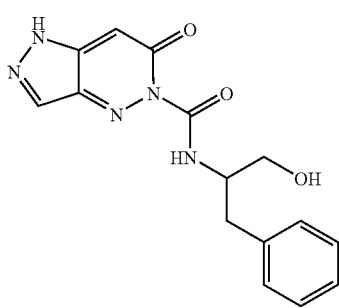 I-29

TABLE 1-continued

Examples of Compounds of Formula I:

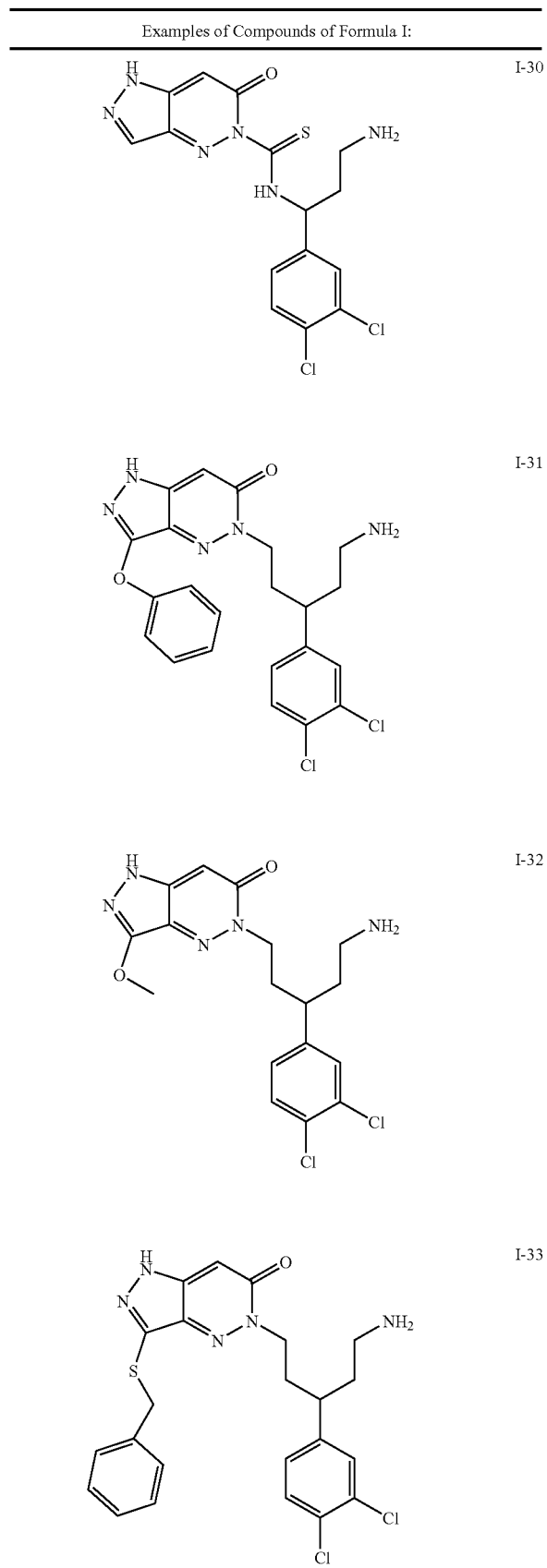

I-30

I-31

I-32

I-33

TABLE 1-continued

Examples of Compounds of Formula I:

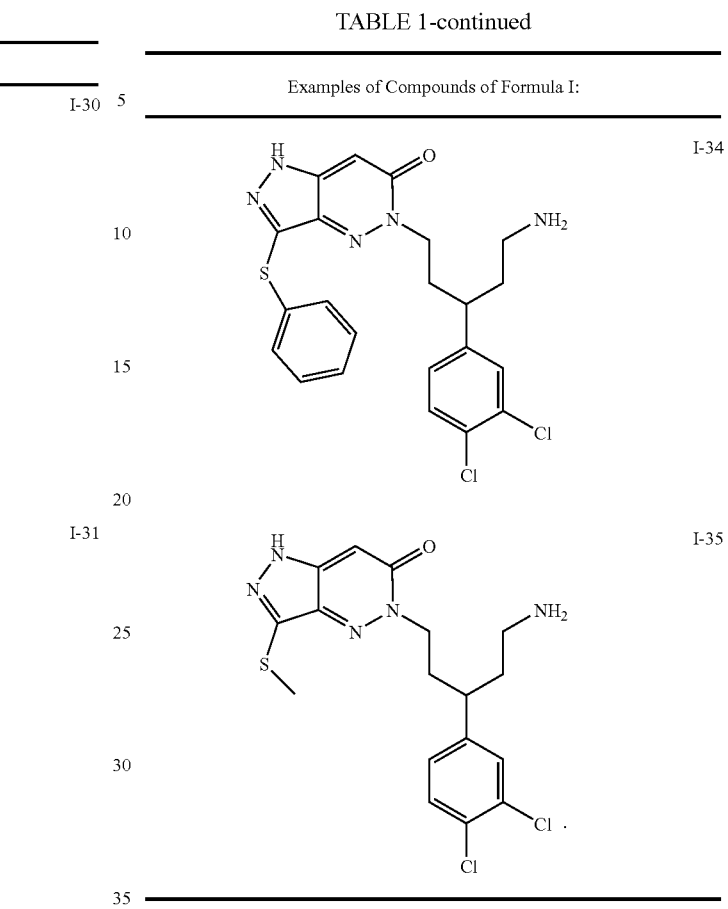

I-34

I-35

III. General Synthetic Methodology:

The compounds of this invention may be prepared in general by methods known to those skilled in the art for analogous compounds. Schemes 1-7 below illustrate synthetic routes to the compounds of the present invention. Other equivalent schemes, which will be readily apparent to the ordinary skilled organic chemist, may alternatively be used to synthesize various portions of the molecule as illustrated by the general scheme below, and the preparative examples that follow.

Scheme 1:

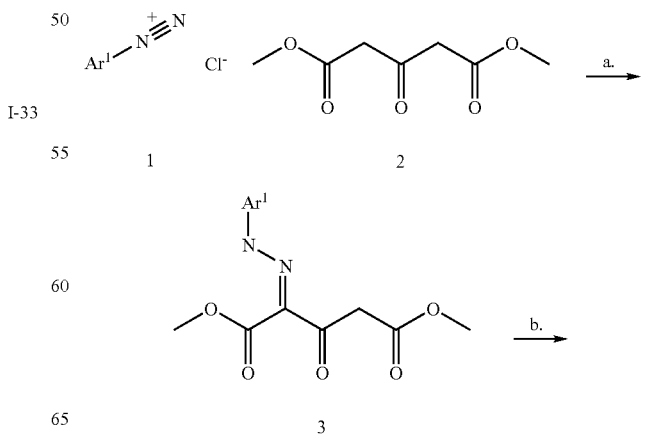

Scheme 2:

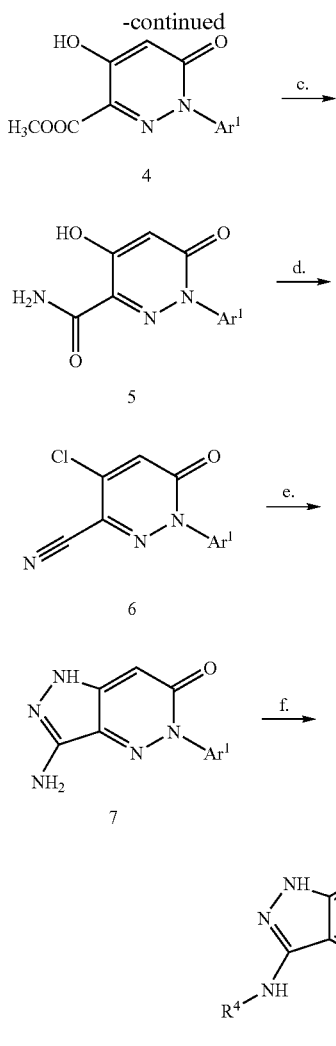
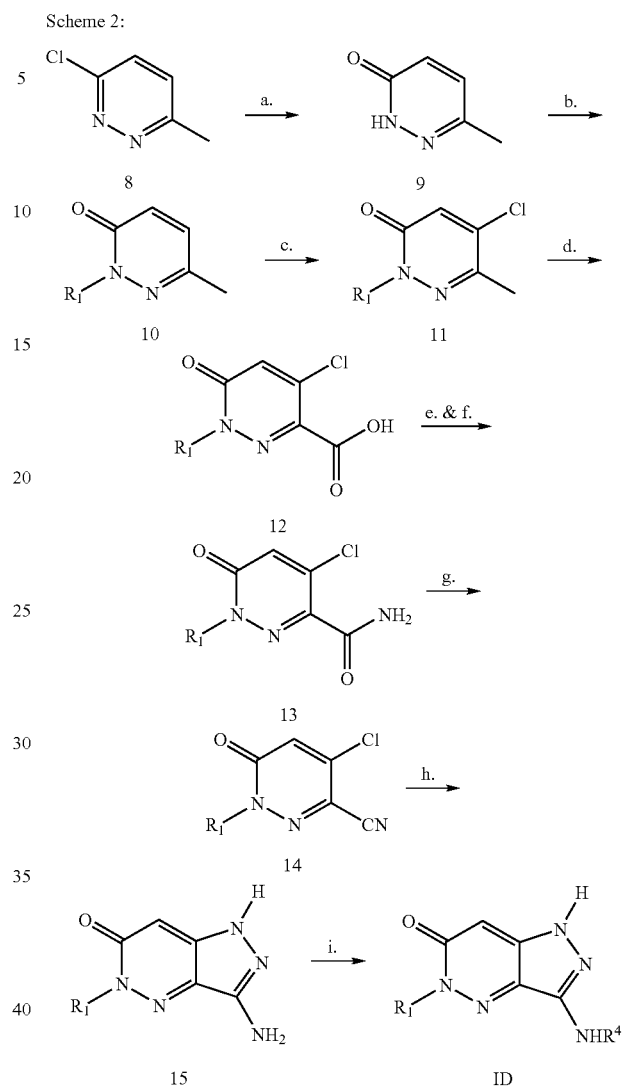

Reagents: (a) NaOAc, EtOH, H₂O; (b) dichlorobenzene, reflux; (c) 7N NH₃ in MeOH; (d) POCl₃, CH₃CN, reflux; (e) H₂NNH₂—H₂O, EtOH, 100°; (f) Ar³—X or R⁴—X, where X=halo.

Scheme 1 above shows a general method for preparing compounds of formula II-D1. For example intermediate 5 may be prepared according to the method of Schober et al., *J. Heterocyclic Chem.*, 26, pp.169-176 (1989) wherein aryldiazonium chloride 1 is reacted with dimethylacetonedicarboxylate 2 to provide intermediate hydrazone 3. Thermal cyclization in refluxing dichlorobenzene provides dihydopyridazine carboxylate 4. Refluxing ammonia in methanol provides amide 5 which is dehydrated and chlorinated by refluxing in excess POCl₃ and acetonitrile to give intermediate 6. Treatment of 6 with excess hydrazine hydrate in refluxing ethanol yields amino pyrazolo-pyridazine 7 which is alkylated with Ar³—X or R—X according to the alkylation procedure of Kawakubo et al., *Chem. Pharm. Bull.*, 35 (6), p.2292-2299 (1987) or Millan et al., *Aust. J. Chem.*, 53, pp.615-618 (2000), or Kohn et al., *J. Med. Chem.*, 34, pp.2444-2452 (1991) or the reductive amination procedure of Taylor et al., *Tetrahedron*, 48, pp.8089-8100 (1992) to provide compounds of formula II-D1.

Reagents: (a) HNO₃; (b) R¹(L)ₘX; (c) Cl₂; (d) K₂Cr₂O₇; (e) (COCl)₂; (f) NH₃; (g) POCl₃; (h) H₂NNH₂—H₂O, EtOH; (i) Ar³—X (where X=halo) or R⁴—Br.

Scheme 2 above shows a general route for the preparation of compounds of formula I wherein R¹ is -(L)ₘR, X is NR, and R⁴ is R. The preparation of intermediate acid 12 from commercially available chloropyrimidine 8 is accomplished according to the procedure of Homer et al., *J. Chem Soc.*, p. 2191 (1948). Intermediate acid 12 is converted to the amide 13 via the acid chloride and displacement with ammonia. Amino pyrazolo-pyridazine 15 is prepared as shown in Scheme 1 and finally alkylation of 15 is accomplished by those procedures described above in Scheme 1 to give compounds of formula ID.

Scheme 3:

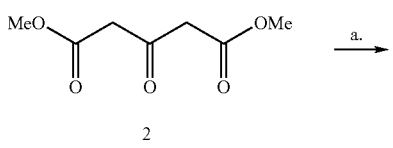

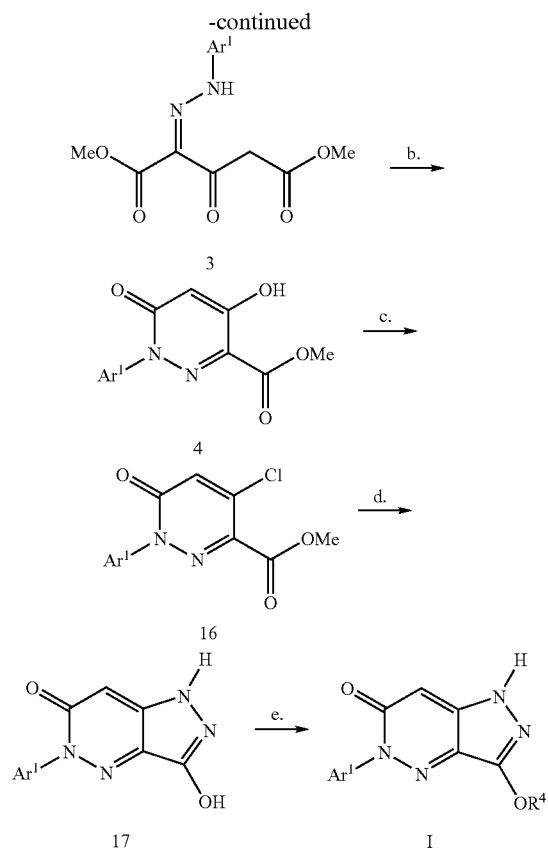

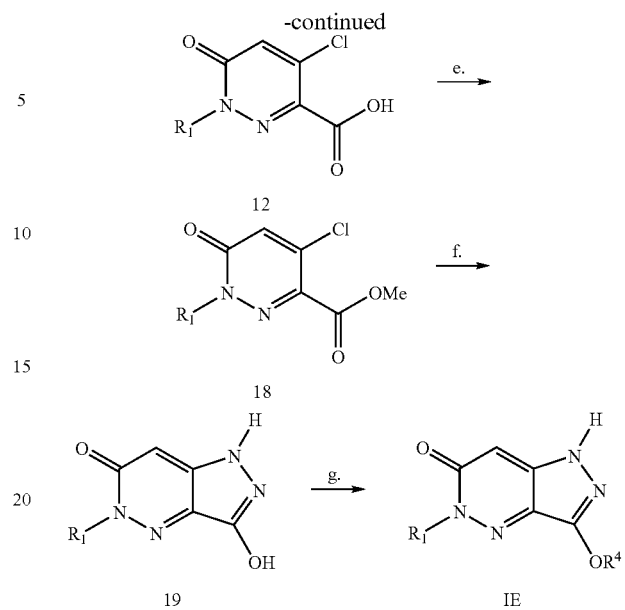

Reagents: (a) Ar¹—N₂⁺Cl⁻, NaOAc, EtOH, H₂O; (b) dichlorobenzene, reflux; (c) POCl₃, CH₃CN, reflux; (d) H₂NNH₂—H₂O, EtOH, 100°; (e) R⁴—X (X=halo).

Scheme 3 above shows a general route for the preparation of compounds of formula I wherein R¹ is -(L)$_m$Ar¹ and m is zero, X is oxygen, and R⁴ is R. Intermediate 4 is prepared from compound 2 as previously described in Scheme 1. Compound 4 is converted to chloride 16 with POCl₃ according to the method of Schober et al., *J. Het. Chem.*, 27, pp.471-477 (1990). Hydroxy pyrazolo-pyridazine 17 is prepared according to the method of Patel et al., *Indian J. Chem.*, 26B, pp.733-744 (1989) and finally alkylation of 17 is accomplished with R⁴ halide according to the method of Oelschlager, et al., *Arch. Pharm.*, 319, pp.939-944 (1986) or Boananomi et al., *Farmaco*, 32, pp.490-501 (1977) or Ardakani, et al., *J. Chem. Soc. Perkin Trans.*, 1, pp.2501-2506 (1983).

Scheme 4:

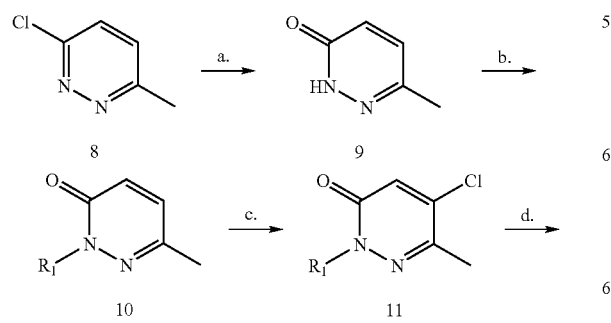

Reagents: (a) HNO₃; (b) R¹(L)$_m$—X (X=halo); (c) Cl₂; (d) K₂Cr₂O₇; (e) MeOH; HCl (f) H₂NNH₂—H₂O, EtOH; (g) R⁴—X (X=halo).

Scheme 4 above shows a general route for preparing compounds of formula IE wherein R¹ is (L)$_m$R, and X is oxygen. Intermediate 12 is prepared according to the method described in Scheme 1. Acid 12 is converted to methyl ester 18 via Fisher esterification and then cyclocondensed with hydrazine hydrate according to the method described in Scheme 3 to give hydroxy pyrazolo-pyridazine 19. O-alkylation is accomplished with R⁴ halide according to the methods described above in Scheme 3.

Scheme 5:

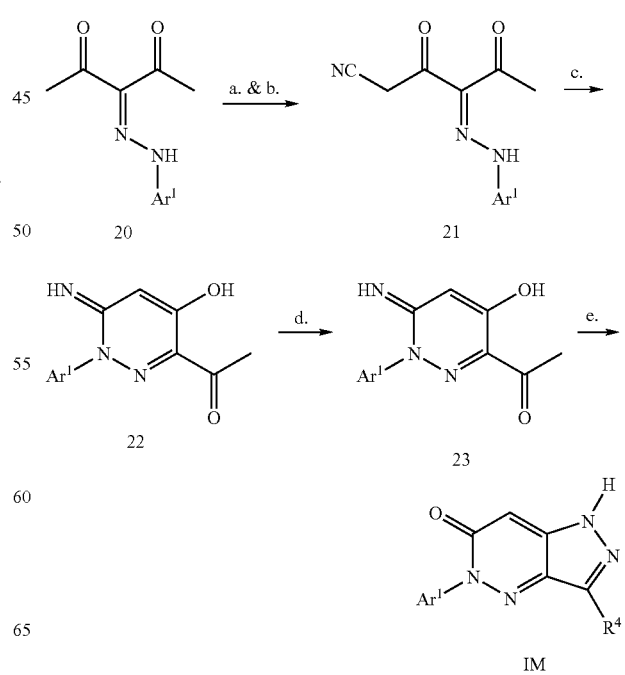

Reagents: (a) Br$_2$; (b) KCN; (c) HOAc; (d) NaNO$_2$; (e) H$_2$NNH$_2$—H$_2$O, EtOH.

Scheme 5 above shows a general route for the preparation of compounds of formula IM wherein X is a valence bond. Aryl hydazone 20 is converted to pyridazine-one 23 according to the method of Patel et al., *Indian J. Chem.*, 26B, pp.733-744 (1989). Cyclo-condensation of 23 to give compounds of formula IM is accomplished according to the method described by Ikesu, S. et al. in Japanese Patent Application JP 04307542, (Konica Co., 1992, 13 pp.).

Scheme 6:

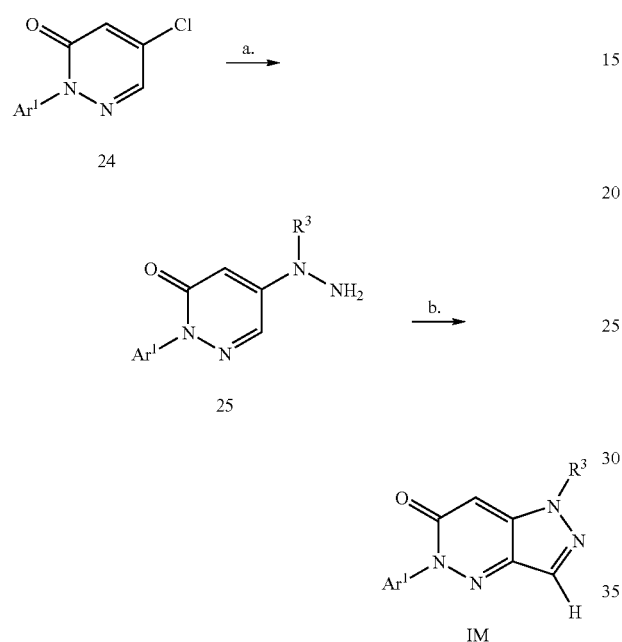

Reagents: (a) R$^3$HNNH$_2$; (b) (CH$_3$)$_2$NCH(OCH$_3$)$_2$

Scheme 6 above shows a general route for the preparation of certain compounds of formula IM wherein X is a valence bond and R$^4$ is hydrogen. Compounds of formula IJ can be prepared from compound 24 according to the methods described by Anderson, P. L. in U.S. Pat. No. 4,004,009 (Sandoz, Inc. 1977, 5 pp.).

Scheme 7:

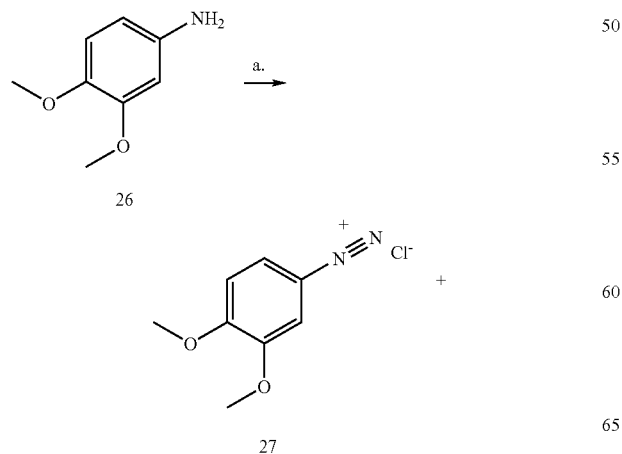

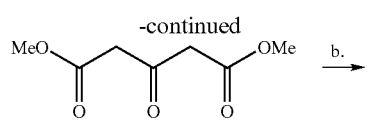

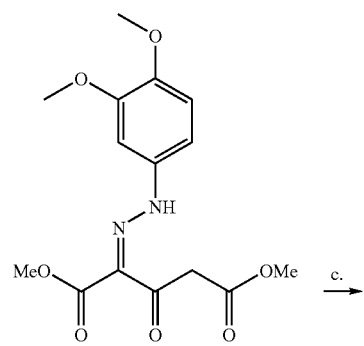

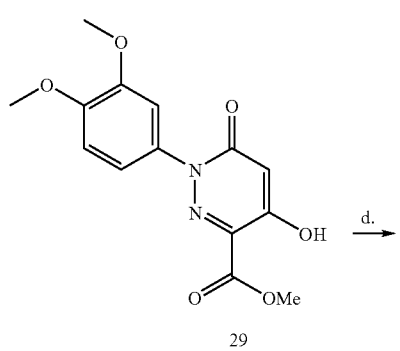

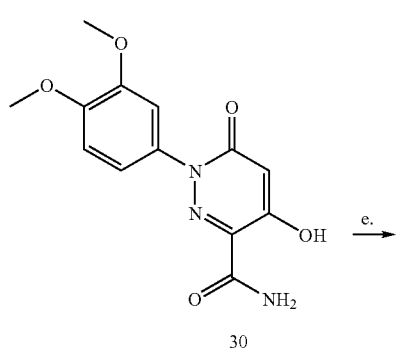

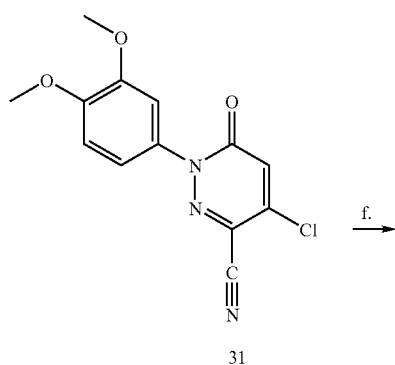

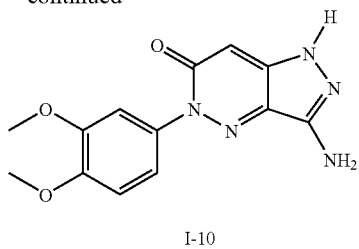

I-10

Reagents: (a) NaNO$_2$, HCl, H$_2$O; (b) NaOAc, EtOH, H$_2$O; (c) dichlorobenzene, reflux; (d) 7N NH$_3$ in MeOH; (e) POCl$_3$, CH$_3$CN, reflux; (f) H$_2$NNH$_2$—H$_2$O, EtOH, 100°.

Scheme 7 above shows a synthetic route for the preparation of compound I-10 of the present invention from commercial aniline 26 using the method described by Schober et al. in *J. Heterocyclic Chem.*, 26, pp.169-176 (1989) and the method described above in Scheme 1.

Although certain exemplary embodiments are depicted and described above and herein, it will be appreciated that a compounds of the invention can be prepared according to the methods described generally above using appropriate starting materials by methods generally available to one of ordinary skill in the art.

The activity of a compound utilized in this invention as an inhibitor of GSK-3 may be assayed in vitro, in vivo or in a cell line. In vitro assays include assays that determine inhibition of either the phosphorylation activity or ATPase activity of activated GSK-3. Alternate in vitro assays quantitate the ability of the inhibitor to bind to GSK-3. Inhibitor binding may be measured by radiolabelling the inhibitor prior to binding, isolating the inhibitor/GSK-3 complex and determining the amount of radiolabel bound. Alternatively, inhibitor binding may be determined by running a competition experiment where new inhibitors are incubated with GSK-3 bound to known radioligands.

According to another embodiment, the invention provides a composition comprising a compound of this invention or a pharmaceutically acceptable salt thereof and a pharmaceutically acceptable carrier, adjuvant, or vehicle. The amount of compound in the compositions of this invention is such that is effective to detectably inhibit a protein kinase, particularly GSK-3, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in GSK-3 activity between a sample comprising said composition and GSK-3 kinase and an equivalent sample comprising GSK-3 kinase in the absence of said composition.

A "pharmaceutically acceptable salt" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite of a compound of the present invention, or residue thereof, is also an inhibitor of GSK-3 kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, flumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention.

For example, neurotrophic factors or other agents for treating neurological or neurodegenerative disorders may be combined with the compounds of this invention to treat neurological and neurodegenerative disorders. Examples of known neurotrophic factors include, but are not limited to, acetylcholinesterase inhibitors, MAO inhibitors, interferons, anti-convulsants, ion channel blockers, riluzole, and anti-Parkinsonian agents.

Examples of known treatments for stroke include Activase®, a recombinant, or genetically engineered, tissue plasminogen activator (rt-PA), heparin, glutamate antagonists, calcium antagonists, opiate antagonists, GABA agonists and antioxidants.

Other examples of agents the compounds of this invention may also be combined with include, without limitation, anti-depressive agents, such as Zoloft®, Prozac®, Paxil®, and Buspar®; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating diabetes such as insulin, insulin analogues, alpha glucosidase inhibitors, biguanides, and insulin sensitizers; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the present invention relates to administering to a patient an additional therapeutic agent selected from a treatment for Alzheimer's Disease (AD), a treatment for Parkinson's Disease, an agent for treating Multiple Sclerosis (MS), a treatment for asthma, an anti-inflammatory agent, an immunomodulatory or immunosuppressive agent, a neurotrophic factor, an agent for treating stroke, an agent for treating cardiovascular disease, an antidepressant, an anti-psychotic agent, or an agent for treating diabetes, wherein:

said additional therapeutic agent is appropriate for the disease being treated; and
said additional therapeutic agent is administered together with said composition as a single dosage form or separately from said composition as part of a multiple dosage form.

According to another embodiment, the invention relates to a method of inhibiting GSK-3 kinase activity in a biological sample comprising the step of contacting said biological sample with a compound of this invention, or composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of GSK-3 kinase activity in a biological sample is useful for a variety of purposes which are known to one of skill in the art. Examples of such purposes include, but are not limited to, blood transfusion, organ-transplantation, biological specimen storage, and biological assays.

According to another embodiment, the invention relates to a method of inhibiting GSK-3 kinase activity in a patient comprising the step of administering to said patient a compound of this invention, or composition comprising said compound.

According to another embodiment, the invention provides a method for treating or lessening the severity of a GSK-3-mediated disease or condition in a patient comprising the step of administering to said patient a composition according to the present invention.

The term "GSK-3-mediated disease" as used herein, means any disease or other deleterious condition or disease in which GSK-3 is known to play a role. Such diseases or conditions include, without limitation, autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease.

According to another embodiment, the present invention relates to a method for treating or lessening the severity of a disease, disorder, or condition selected from an autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease, in a patient in need thereof, comprising administering to said patient a compound of the present invention or composition thereof.

According to another embodiment, the present invention relates to a method for treating or lessening the severity of a disease or condition selected from allergy, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), an injury due to head trauma, schizophrenia, anxiety, bipolar disorder, tauopothy, a spinal cord or peripheral nerve injury, myocardial infarction, cardiomyocyte hypertrophy, glaucoma, attention deficit disorder (ADD), depression, a sleep disorder, reperfusion/ischemia, stroke, an angiogenic disorder, or baldness, wherein said method comprises administering to a patient in need thereof a compound of the present invention or composition thereof.

According to another embodiment, the method of the present invention relates to treating or lessening the severity of stroke.

According to another embodiment, the method of the present invention relates to treating or lessening the severity of Alzheimer's disease.

According to another embodiment, the method of the present invention relates to treating or lessening the severity of a neurodegenerative or neurological disorder.

According to another embodiment, the method of the present invention relates to decreasing sperm motility in a male patient.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another embodiment, includes a composition for coating an implantable device comprising a compound of the present invention as described generally above, and in classes and subclasses herein, and a carrier suitable for coating said implantable device. In still another embodiment, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

In order that the invention described herein may be more fully understood, the following examples are set forth. It should be understood that these examples are for illustrative purposes only and are not to be construed as limiting this invention in any manner.

EXAMPLES $^1$H-NMR spectra were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using chromatography. Mobile phase for all mass spec. analysis consisted of acetonitrile-water mixtures with 0.2% formic acid as a modifier.

As used herein, the term "$R_t$(min)" refers to the HPLC retention time, in minutes, associated with the compounds of this invention obtained from the mass spec. analysis.

Chemical naming for selected compounds herein was accomplished using the naming program provided by CambridgeSoft Corporations ChemDraw Ultra®, version 7.0.1

Example 1

2-[(3,4-Dimethoxy-phenyl)-hydrazono]-3-oxo-pentanedioic acid dimethyl ester (28)

A mixture of 2.5 ml of concentrated HCl, 5 ml of $H_2O$, and 5.523 mmoles of aniline (26) was treated with a solution of sodium nitrite 381 mg (5.52 mmoles) in 5 ml of water in an ice bath. This reaction was stirred for two hours to give crude diazonium chloride (27) which was not isolated. The crude diazonium salt solution was poured into a mixture of 961 mg of dimethyl acetonedicarboxylate (2) in 3 ml of ethanol and 3 g of sodium acetate in 10 ml of water with vigorous stirring. Product precipitated immediately. The reaction was allowed to stir for an additional 2 hours, then filtered and dried to give 1.363 g of the desired hydrazone (28) as a solid. MS$^+$: m/e=339.1 (M+H).

Example 2

1-(3,4-Dimethoxy-phenyl)-4-hydroxy-6-oxo-1,6-dihydro-pyridazine-3-carboxylic acid methyl ester (29)

The hydrazone (28) (500 mg) was dissolved in dichlorobenzene and heated to reflux in a sealed tube for 4 hours. The reaction was allowed to cool and cyclohexane was added dropwise to crystallize the desired product. Filtration and drying in vacuo yielded the desired dihydropyridazine ester (29) (295 mg) as a solid. MS$^+$: m/e=307.0 (M+H).

Example 3

1-(3,4-Dimethoxy-phenyl)-4-hydroxy-6-oxo-1,6-dihydro-pyridazine-3-carboxylic acid amide (30)

The pyridazine (29) (295 mg) was dissolved in 3 ml of 7N $NH_3$ in methanol and heated to reflux in a sealed tube for 4 hours. The reaction was allowed to cool, neutralized with acetic acid, and concentrated to dryness to give 266 mg of desired amide (30) as a solid. MS$^+$: m/e=292.0 (M+H).

Example 4

4-Chloro-1-(3,4-dimethoxy-phenyl)-6-oxo-1,6-dihydro-pyridazine-3-carbonitrile (31)

The starting amide (30) (190 mg) was dissolved in 1 ml of $CH_3CN$, treated with 1 ml of phosphorus oxychloride, and heated to reflux. After 18-20 hours the reaction was complete by HPLC. The reaction mixture was poured into ice and stirred for one hour. The product was extracted with ethyl acetate, the organic phase dried over magnesium sulfate, filtered, and concentrated to dryness. This material was then purified by normal phase column $SiO_2$ chromatography affording 90 mg of desired nitrile chloride (31) as a solid. MS$^+$: m/e=292.0 (M+H), $^1$H-NMR (500 MHz, MeOH-$d_4$): d 7.40 (s, 1H), 7.18 (s, 1H), 7.12 (d, 1H), 7.08 (d, 1H), 3.90 (s, 3H), 3.85 (s, 3H), ppm.

Example 5

3-Amino-5-(3,4-dimethoxy-phenyl)-1,5-dihydro-pyrazolo[4,3-c]pyridazine-6-one (I-10)

The starting chloride (31) (190 mg) was dissolved in 500 μl of ethanol. 5 equivalents of hydrazine hydrate were added and the reaction mixture heated in a sealed tube at 100° C. for 18 hours. HPLC showed the reaction to be complete. The reaction was concentrated to dryness and purified by normal phase $SiO_2$ chromatography eluting with (1:1) ethyl acetate-hexanes going to 100% ethyl acetate to give after drying 25 mg of desired product (I-10) as a solid. MS$^+$: m/e=288.0 (M+H)$^+$, $^1$H-NMR (500 MHz, MeOH-$d_4$): d 7.17 (s, 1H), 7.11 (d, 1H), 7.07 (d, 1H), 6.37 (s, 1H), 3.90 (s, 3H), 3.85 (s, 3H), ppm.

Example 6

5-(4-Methoxy-phenyl)-3-(pyrimidin-2-ylamino)-1,5-dihydro-pyrazolo[4,3-c]pyridazin-6-one (I-17)

To 3-amino-5-(4-methoxy-phenyl)-1,5-dihydro-pyrazolo[4,3-c]pyridazin-6-one (purchased from Bionet, 67.6 mg, 0.2628 mmoles) in N-methylpyrrolidinone (263 uL) was added 2-chloro-pyrimidine (15.1 mg, 0.5 eq). The reaction was stirred for 5 hours at 130° C. to give crude desired product as evidenced by mass spectrometry. The reaction was diluted with methanol (2 ml) and purified by reverse phase chromatography to give 25 mg (28%) of pure 5-(4-methoxy-phenyl)-3-(pyrimidin-2-ylamino)-1,5-dihydro-pyrazolo[4,3-c]pyridazin-6-one (I-17) as a solid. LC/MS: $t_{ret}$=2.13 min, M+H$^+$=336.1.

Table 2 below depicts exemplary mass spectral and $^1$H-NMR data for certain compounds of this invention:

TABLE 2

| Compound | Mass Spec. (M + H)$^+$ | $R_t$(min) | $^1$H-NMR |
|---|---|---|---|
| I-1 | 258.0 | 1.59 | Methanol-d4: d 7.4(m, 1H), 7.12 (m, 2H), 7.04(dd, 1H), 6.35(s, 1H), 3.33(s, 3H) ppm. |
| I-2 | 228.0 | 1.38 | Methanol-d4: d 7.6-7.4(m, 5H), 6.35(s, 1H) ppm. |
| I-3 | 296.0 | 2.1 | Methanol-d4: d 7.72(m, 1H), 7.52 (m, 2H), 6.35(s, 1H) ppm. |
| I-4 | 320.1 | 2.63 | Methanol-d4: d 7.54(d, 2H), 7.38 (t, 2H), 7.16(t, 1H), 7.08(m, 4H), 6.35(s, 1H) ppm. |
| I-5 | 242.1 | 1.80 | DMSO-d6: d 11.17(s, 1H), 7.41 (d, 2H), 7.28(d, 2H), 6.18(s, 1H), 6.1(s, 2H), 2.36(s, 3H) ppm. |
| I-6 | 484.1 | 2.17 | |
| I-7 | 273.0 | 1.59 | DMSO-d6: d 11.2(s, 1H), 8.51(s, 1H), 8.3(d, 1H), 8.13(d, 1H), 7.82 |

TABLE 2-continued

| Compound | Mass Spec. (M + H)+ | R_t(min) | 1H-NMR |
|---|---|---|---|
| I-8 | 262.0 | 1.80 | (t, 1H), 6.25(s, 1H), 6.18(s, 2H) ppm. DMSO-d6: d 11.22(s, 1H), 7.65-7.5 (m, 3H), 6.2-6.05(m, 3H) ppm. |
| I-9 | 307.0 | | DMSO-d6: d 11.25(s, 1H), 8.03 (s, 1H), 7.9(d, 1H), 7.82(d, 1H), 7.71(m, 1H), 7.53(m, 2H), 6.22 (s, 1H), 6.15(s, 2H) ppm. |
| I-10 | 288.0 | 1.21 | Methanol-d4: d 7.17(d, 1H), 7.11 (d, 1H), 7.07(s, 1H), 6.37(s, 1H), 3.9(s, 3H), 3.85(s, 3H) ppm. |
| I-11 | 336.1 | 2.09 | |
| I-12 | 374.1 | 2.58 | |
| I-13 | 374.2 | 2.67 | |
| I-14 | 398.2 | 3.03 | |
| I-15 | 262.0 | 1.17 | DMSO-d6: d 11.2(s, 1H), 7.68 (dd, 1H), 7.61(dd, 1H), 7.53(m, 2H), 6.22(s, 1H), 6.16(s, 2H) ppm. |
| I-16 | 258.1 | 1.05 | DMSO-d6: d 11.2(s, 1H), 7.46(t, 1H), 7.33(d, 1H), 7.2(d, 1H), 7.07 (t, 1H), 6.4-6.0(bs, 2H), 6.14(s, 1H), 3.73(s, 3H) ppm. |
| I-17 | 336.1 | 2.13 | |
| I-18 | 273.0 | 1.63 | DMSO-d6: d 11.25(s, 1H), 8.39 (d, 2H), 7.95(d, 2H), 6.2(m, 3H) ppm. |

Example 7

Inhibition of GSK-3

Compounds were screened for their ability to inhibit GSK-3β (AA 1-420) activity using a standard coupled enzyme system (Fox et al. *Protein Sci.* 7, p.2249 (1998)). Reactions were carried out in a solution containing 100 mM HEPES (pH 7.5), 10 mM $MgCl_2$, 25 mM NaCl, 300 µM NADH, 1 mM DTT and 1.5% DMSO. Final substrate concentrations in the assay were 20 µM ATP (Sigma Chemicals, St Louis, Mo.) and 300 µM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of interest. The assay stock buffer solution (175 µl) was incubated in a 96 well plate with 5 µl of the test compound of interest at final concentrations spanning 0.002 µM to 30 µM at 30° C. for 10 min. Typically, a 12 point titration was conducted by preparing serial dilutions (from 10 mM compound stocks) with DMSO of the test compounds in daughter plates. The reaction was initiated by the addition of 20 µl of ATP (final concentration 20 µM). Rates of reaction were obtained using a Molecular Devices Spectramax plate reader (Sunnyvale, Calif.) over 10 min at 30° C. The $K_i$ values were determined from the rate data as a function of inhibitor concentration.

The following compounds were shown to have $K_i$ values less than 4.0 µM for GSK-3: I-1, I-2, I-4, I-5, I-6, I-7, I-8, and I-9

We claim:
1. A compound of formula I:

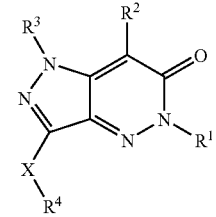

or a pharmaceutically acceptable salt or mixtures thereof, wherein $R^1$ is selected from $-(L)_m R$, $-(L)_m Ar^1$, or $-(L)_m Cy^1$; L is an optionally substituted $C_{1-6}$ alkylidene chain wherein up to two non-adjacent methylene units of L are optionally replaced by O, NR, NRCO, NRCS, NRCONR, NRCSNR, $NRCO_2$, CO, $CO_2$, CONR, CSNR, OC(O)NR, $SO_2$, $SO_2NR$, $NRSO_2$, $NRSO_2NR$, C(O)C(O), or $C(O)CH_2C(O)$; m is 0 or 1; $Ar^1$ is an optionally substituted aryl group selected from a 3-8 membered monocyclic or an 8-10 membered bicyclic ring having 0-5 heteroatoms independently selected from nitrogen, oxygen, or sulfur; and $Cy^1$ is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur, wherein $Ar^1$ and $Cy^1$ are each independently optionally substituted with y occurrences of $Z-R^Y$; wherein Z is a bond or is a $C_1-C_6$ alkylidene chain wherein up to two non-adjacent methylene units of Z are optionally replaced by CO, $CO_2$, COCO, CONR, CSNR, OCONR, NRNR, NRNRCO, NRCO, NRCS, $NRCO_2$, NRCONR, NRCSNR, SO, $SO_2$, $NRSO_2$, $SO_2NR$, $NRSO_2NR$, O, S, or NR; and each occurrence of $R^Y$ is independently selected from R', halogen, $NO_2$, CN, OR', SR', $N(R')_2$, NR'C(O)R', NR'C(S)R', NR'C(O) $N(R')_2$, $NR'C(S)N(R')_2$, $NR'CO_2R'$, C(O)R', $CO_2R'$, OC(O)R', $C(O)N(R')_2$, $C(S)N(R')_2$, $OC(O)N(R')_2$, SOR', $SO_2R'$, $SO_2N(R')_2$, $NR'SO_2R'$, $NR'SO_2N(R')_2$, C(O)C(O)R', or $C(O)CH_2C(O)R'$; and y is 0-5

$R^2$ is selected from halogen, $NO_2$, —SR, —$N(R)_2$, $-(T)_n R$, or $-(T)_n Ar^2$ wherein T is an optionally substituted $C_{1-4}$ alkylidene chain wherein up to two non-adjacent methylene units of T are optionally replaced by O, NR, NRCO, NRCS, NRCONR, NRCSNR, $NRCO_2$, CO, $CO_2$, CONR, CSNR, OC(O)NR, $SO_2$, $SO_2NR$, $NRSO_2$, $NRSO_2NR$, C(O)C(O), or $C(O)CH_2C(O)$; n is 0 or 1; $Ar^2$ is an optionally substituted aryl group selected from a 5-6 membered monocyclic or an 8-10 membered bicyclic ring having 0-5 heteroatoms independently selected from nitrogen, oxygen, or sulfur wherein $Ar^2$ is independently optionally substituted with up to five substituents selected from $Q-R^X$; wherein Q is a bond or is a $C_1-C_6$ alkylidene chain wherein up to two non-adjacent methylene units of Q are optionally replaced by CO, $CO_2$, COCO, CONR, CSNR, OCONR, NRNR, NRNRCO, NRCO, NRCS, $NRCO_2$, NRCONR, NRCSNR, SO, $SO_2$, $NRSO_2$, $SO_2NR$, $NRSO_2NR$, O, S, or NR; and each occurrence of $R^X$ is independently selected from R', halogen, $NO_2$, CN, OR', SR', $N(R')_2$, NR'C(O)R', NR'C (S)R', $NR'C(O)N(R')_2$, $NR'C(S)N(R')_2$, $NR'CO_2R'$, C(O)R', CO₂R', OC(O)R', C(O)N(R')₂, C(S)N(R')₂, OC(O)N(R')₂, SOR', SO₂R', SO₂N(R')₂, NR'SO₂R', NR'SO₂N(R')₂, C(O)C(O)R', or C(O)CH₂C(O)R';

R³ is hydrogen or an optionally substituted $C_{1-4}$ aliphatic group;

X is selected from a valence bond, O, S, or NR;

R⁴ is selected from —R, —(U)-Ar³, or —(U)$_j$Cy³; U is an optionally substituted $C_{1-6}$ alkylidene chain wherein up to two non-adjacent methylene units of U are optionally replaced by O, NR, NRCO, NRCS, NRCONR, NRCSNR, NRCO₂, CO, CO₂, CONR, CSNR, OC(O)NR, SO₂, SO₂NR, NRSO₂, NRSO₂NR, C(O)C(O), or C(O)CH₂C(O); j is 0 or 1; Ar³ is an optionally substituted aryl group selected from a 3-8 membered monocyclic or an 8-10 membered bicyclic ring having 0-5 heteroatoms independently selected from nitrogen, oxygen, or sulfur; and Cy³ is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur, wherein Ar³ and Cy³ are each independently optionally substituted with up to five substituents selected from Y—R$^Z$; wherein Y is a bond or is a $C_1$-$C_6$ alkylidene chain wherein up to two non-adjacent methylene units of Y are optionally replaced by CO, CO₂, COCO, CONR, CSNR, OCONR, NRNR, NRNRCO, NRCO, NRCS, NRCO₂, NRCONR, NRCSNR, SO, SO₂, NRSO₂, SO₂NR, NRSO₂NR, O, S, or NR; and each occurrence of R$^Z$ is independently selected from R', halogen, NO₂, CN, OR', SR', N(R')₂, NR'C(O)R', NR'C(S)R', NR'C(O)N(R')₂, NR'C(S)N(R')₂, NR'CO₂R', C(O)R', CO₂R', OC(O)R', C(O)N(R')₂, C(S)N(R')₂, OC(O)N(R')₂, SOR', SO₂R', SO₂N(R')₂, NR'SO₂R', NR'SO₂N(R')₂, C(O)C(O)R', or C(O)CH₂C(O)R'; or wherein R⁴ and R, taken together with the nitrogen form an optionally substituted 5-8 membered heterocyclyl or heteroaryl ring having 1-3 heteroatoms independently selected from nitrogen, oxygen, or sulfur;

each occurrence of R is independently selected from hydrogen or an optionally substituted $C_{1-6}$ aliphatic group, or two R on the same nitrogen are taken together with the nitrogen to form a 5-8 membered heterocyclyl or heteroaryl ring having 1-3 heteroatoms independently selected from nitrogen, oxygen, or sulfur; and each occurrence of R' is independently selected from hydrogen or an optionally substituted group selected from $C_{1-6}$ aliphatic, $C_{6-10}$ aryl, a heteroaryl ring having 5-10 ring atoms, or a heterocyclyl ring having 3-10 ring atoms, or wherein two R on the same nitrogen are taken together with the nitrogen to form a 5-8 membered heterocyclyl or heteroaryl ring having 1-3 heteroatoms independently selected from nitrogen, oxygen, or sulfur, provided that:

a) when X is NR; R, R³, and R⁴ are each hydrogen; R² is -(T)$_n$R wherein n is 0 and R is hydrogen; and R¹ is -(L)$_m$Ar¹ wherein m is 0; then Ar¹ is not:
  i) 4-Cl or 4-OMe phenyl; or
  ii) 3-CF₃ phenyl;

d) when X is a valence bond; R⁴ is hydrogen; R³ is CH₃; R² is either chloro or hydrogen; and R¹ is -(L)$_m$Ar¹ wherein m is 0, then Ar¹ is not 3-trifluoromethyl phenyl or 2-fluoro-5-trifluoromethyl phenyl;

f) when X is a valence bond; R⁴ is methyl; R² is -(T)$_n$R wherein n is 0 and R is hydrogen; R³ is hydrogen; and R¹ is -(L)$_m$Ar¹ wherein m is 0; then Ar¹ is not 4-tolyl;

g) 2-[2,4-bis(1,1-dimethylpropyl)phenoxy]-N-[4-[1,6-dihydro-3-methyl-7-(4-nitrophenoxy)-6-oxo-5H-pyrazolo[4,3-c]pyridazin-5-yl]phenyl]-butanamide is excluded.

2. The compound according to claim 1, wherein R¹ is -(L)$_m$Ar¹ and Ar¹ is selected from one of the following groups:

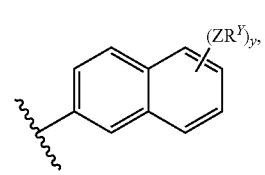
1-1

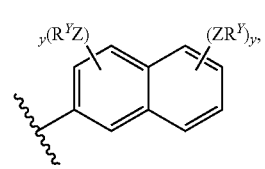
1-2

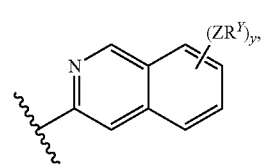
1-3

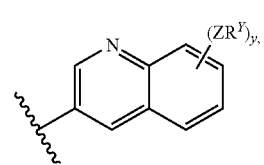
1-4

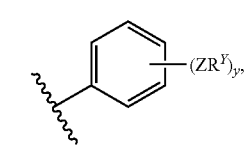
1-5

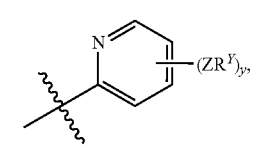
1-6

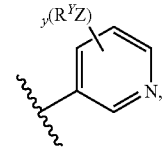
1-7

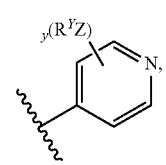
1-8

-continued
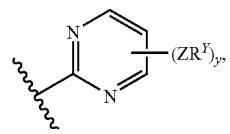 1-9
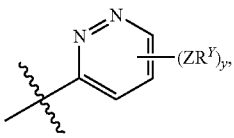 1-10
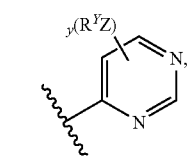 1-11
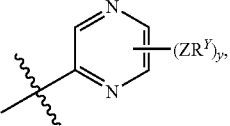 1-12
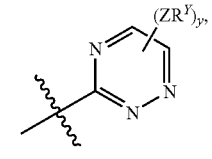 1-13
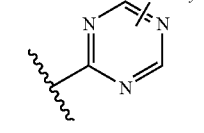 1-14
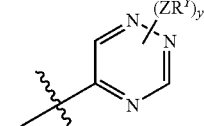 1-15
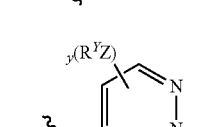 1-16
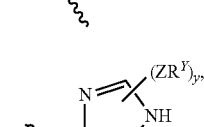 1-17
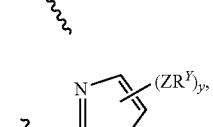 1-18
-continued
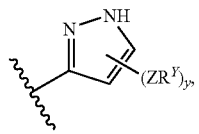 1-19
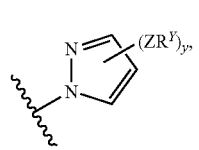 1-20
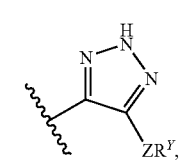 1-21
 1-22
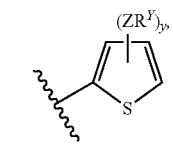 1-23
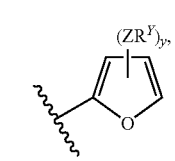 1-24
 1-25
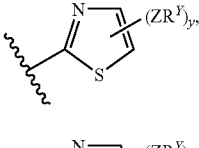 1-26
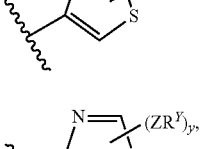 1-27
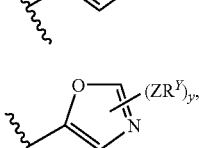 1-28
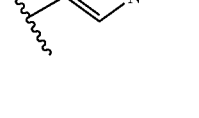 1-29

-continued
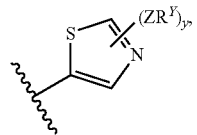 1-30
 1-31
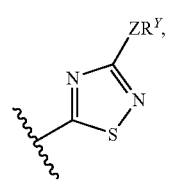 1-32
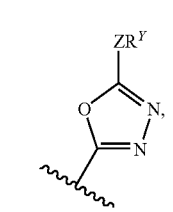 1-33
 1-34
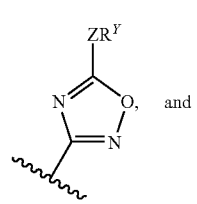 1-35
 1-36
3. The compound according to claim 2, wherein $Ar^1$ is selected from one of the following groups:
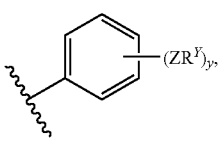 1-5
-continued
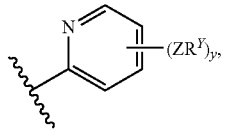 1-6
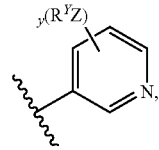 1-7
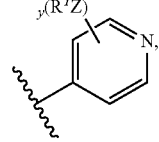 1-8
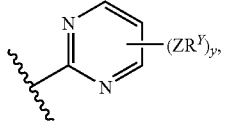 1-9
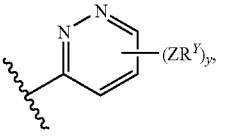 1-10
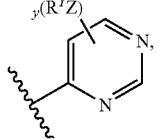 1-11
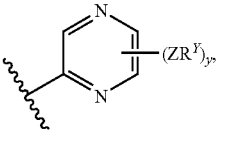 1-12
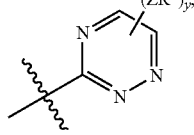 1-13
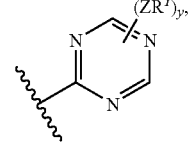 1-14
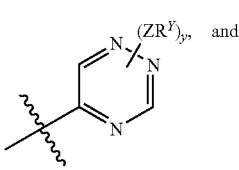 1-15

-continued 1-16

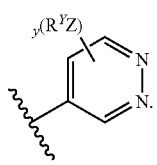

4. The compound according to claim 3, wherein Ar¹ is selected from one of the following groups:

1-5

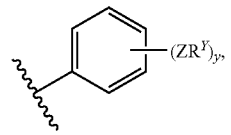

1-6

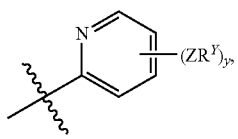

1-7

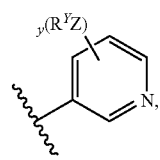

1-8

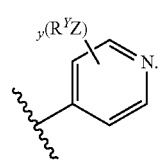

5. The compound according to claim 2, wherein R¹ is -(L)$_m$-Ar¹, m is 1 and compounds have the formula IA-3:

IA-3

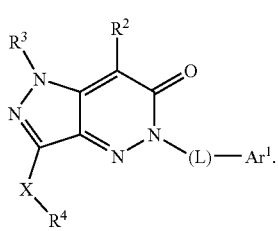

6. The compound according to claim 2, wherein Ar¹ is phenyl with 0-5 occurrences of ZR$^Y$ and compounds have the formula IA-1-5:

IA-1-5

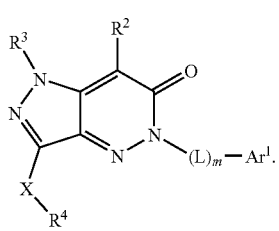

7. The compound according to claim 1, wherein R¹ is -(L)$_m$-Cy¹ and compounds have the formula IA-2:

IA-2

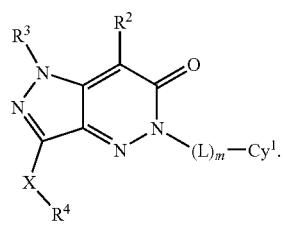

8. The compound according to claim 7, wherein Cy¹ is selected from one of the following groups:

2-1

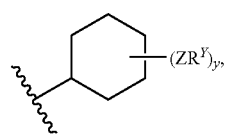

2-2

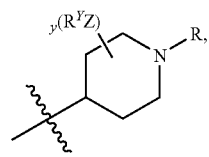

2-3

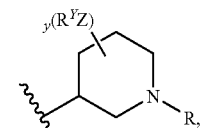

2-4

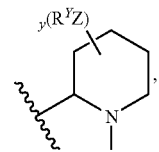

2-5

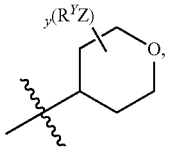

2-6

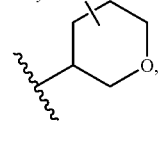

2-7

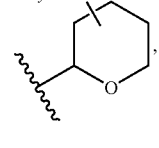

2-8

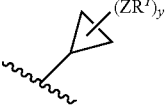

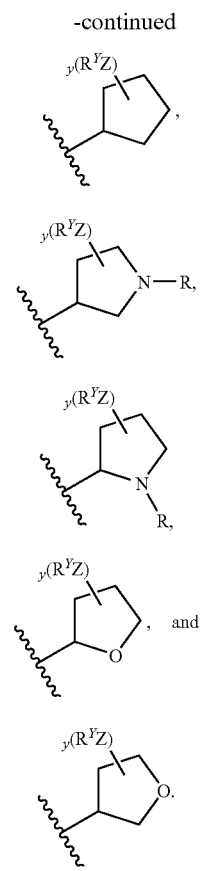

9. The compound according to claim 2, wherein L is an optionally substituted $C_{1-6}$ straight or branched alkylidene chain wherein one methylene unit of L is optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O) and m is 1.

10. The compound according to claim 9, wherein L is an optionally substituted $C_{1-6}$ straight or branched alkylidene chain wherein one methylene unit of L is optionally replaced by CO, CO$_2$, CONR, CSNR, SO$_2$NR, and m is 1.

11. The compound according to claim 1, wherein $R^1$ is -(L)$_m$R, L is an optionally substituted $C_{1-6}$ straight or branched alkylidene chain wherein one methylene unit of L is optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C (O), R is an optionally substituted $C_{1-6}$ aliphatic group and m is 1.

12. The compound according to claim 1, wherein $R^2$ is selected from halogen, NO$_2$, CN, —SR, —N(R)$_2$, or -(T)$_n$R, wherein R is selected from hydrogen or an optionally substituted $C_{1-6}$ aliphatic group, or two R on the same nitrogen are taken together with the nitrogen to form a 5-8 membered heterocyclyl or heteroaryl ring having 1-3 heteroatoms independently selected from nitrogen, oxygen, or sulfur.

13. The compound according to claim 12, wherein $R^2$ is selected from —N(R)$_2$, or -(T)$_n$R, wherein n is 0, and R is selected from hydrogen or an optionally substituted $C_{1-6}$ aliphatic group.

14. The compound according to claim 13, wherein $R^2$ is -(T)$_n$R, wherein n is 0, and R is selected from hydrogen, CH$_3$, or CF$_3$.

15. The compound according to claim 1, wherein $R^2$ is -(T)$_n$R, wherein n is 0, R is hydrogen, and compounds have the formula IB:

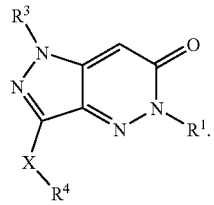

IB

16. The compound according to claim 1, wherein $R^3$ is hydrogen, methyl, ethyl, propyl, or isopropyl.

17. The compound according to claim 16, wherein $R^3$ is hydrogen or methyl.

18. The compound according to claim 1, wherein $R^3$ is hydrogen and compounds have the formula IC:

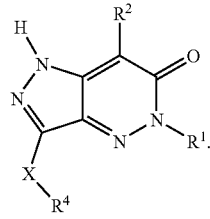

IC

19. The compound according to claim 1, wherein X is selected from a valence bond or NR.

20. The compound according to claim 19, wherein X is NR and R is hydrogen.

21. The compound according to claim 1, wherein X is NR, R is hydrogen, and compounds have the formula ID:

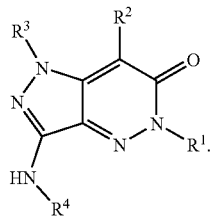

ID

22. The compound according to claim 1, wherein X is O and compounds have the formula IE:

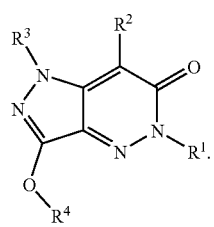

IE

23. The compound according to claim 1, wherein X is S and compounds have the formula IF:
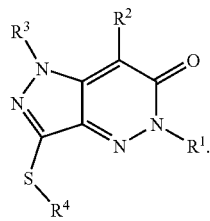
IF
24. The compound according to claim 1, wherein X is NR, R is hydrogen, $R^4$ is —U—$Ar^3$ and compounds have the formula IG:
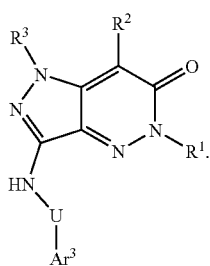
IG
25. The compound according to claim 1, wherein $R^4$ is —(U)—$Ar^3$ and $Ar^3$ is selected from one of the following groups:
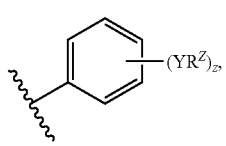
1-5-a
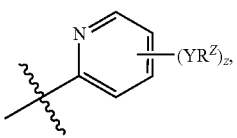
1-6-a
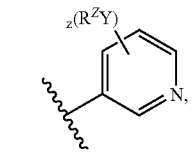
1-7-a
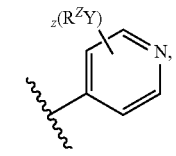
1-8-a
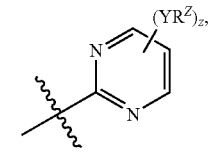
1-9-a
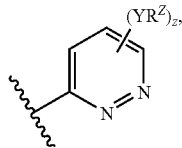
1-10-a
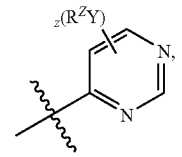
1-11-a
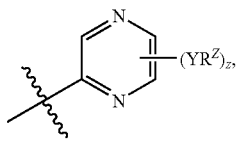
1-12-a
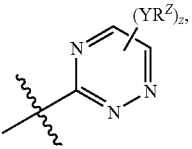
1-13-a
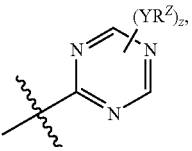
1-14-a
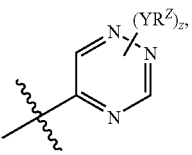
1-15-a
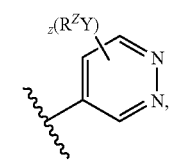
1-16-a
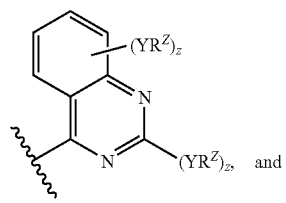
1-37
and
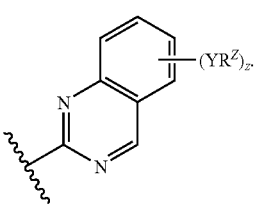
1-38

26. The compound according to claim 25, wherein Ar³ is selected from one of the following groups:
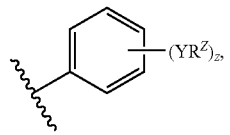
1-5-a
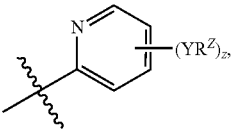
1-6-a
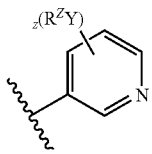
1-7-a
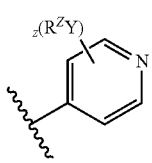
1-8-a
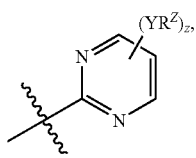
1-9-a
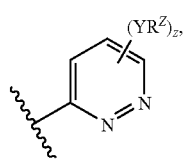
1-10-a
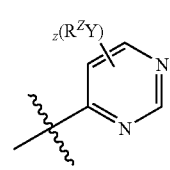
1-11-a
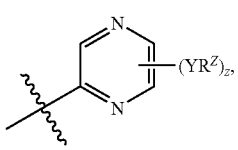
1-12-a
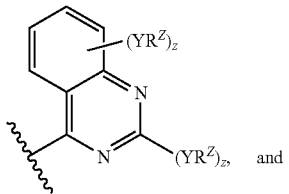
1-37
and
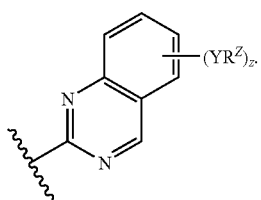
1-38
27. The compound according to claim 26, wherein Ar³ is selected from one of the following groups:
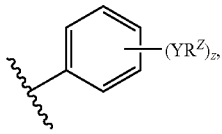
1-5-a
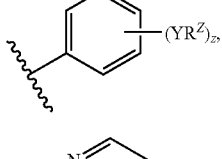
1-6-a
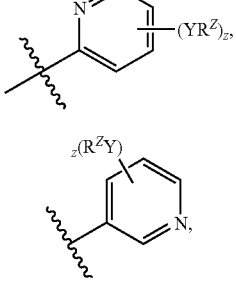
1-7-a
1-8-a
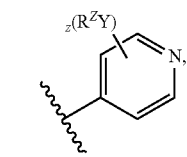
1-9-a
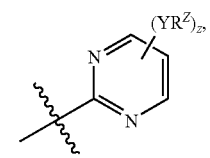
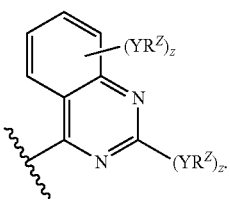
1-37
28. The compound according to claim 1, wherein R⁴ is —(U)—Ar³ and compounds have one of the following formulas:
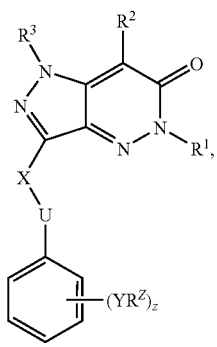
IE IF
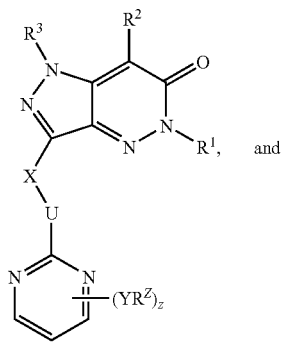
and
IG
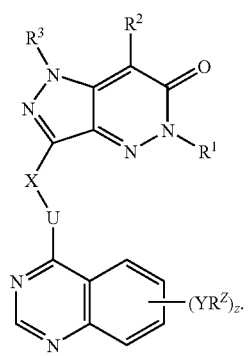
29. The compound according to claim 1, wherein X is NR, R is hydrogen, $R^4$ is $—(U)_jCy^3$ and compounds have the formula IG-1:
IG-1
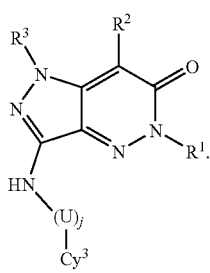
30. The compound according to claim 29, wherein $Cy^3$ is selected from one of the following groups:
2-1
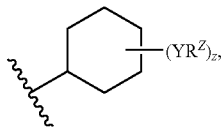
2-2
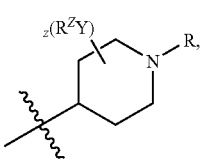
2-3
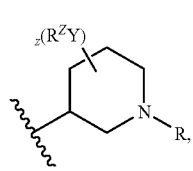
-continued
2-4
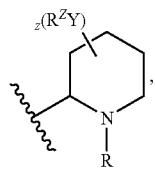
2-5
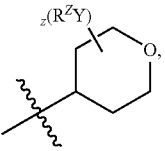
2-6
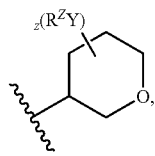
2-7
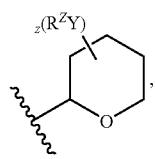
2-8
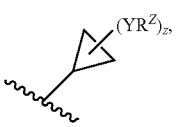
2-9
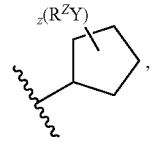
2-10
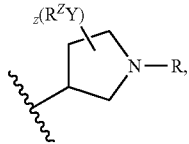
2-11
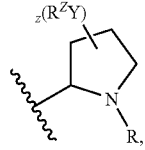
2-12
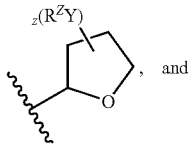
and
2-13
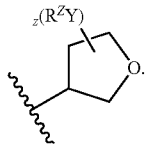

31. The compound according to claim 1, wherein X is NR, R and R⁴ are hydrogen, and compounds have the formula IL:

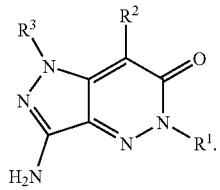

IL

32. The compound according to claim 1, wherein X is a valence bond and compounds have the formula IM:

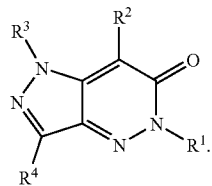

IM

33. The compound according to claim 1, wherein R⁴ is R and R is an optionally substituted $C_{1-6}$ aliphatic group.

34. The compound according to claim 1, wherein y is 0-5, and Ar¹ and Cy¹ are independently substituted with 0-5 occurrences of $ZR^Y$.

35. The compound according to claim 1, wherein y is 0-5, and Ar³ and Cy³ are independently substituted with 0-5 occurrences of $YR^Z$.

36. The compound according to claim 1, wherein y is 0, and Ar¹ is unsubstituted.

37. The compound according to claim 1, wherein $ZR^Y$ and $YR^Z$ groups are each independently halogen, NO₂, CN, or an optionally substituted group selected from $C_{1-4}$ aliphatic, aryl, aralkyl, —N(R')₂, —CH₂N(R')₂, —OR', —CH₂OR', —SR', —CH₂SR', —COOR', or —S(O)₂N(R')₂.

38. The compound of claim 30, wherein $ZR^Y$ and $YR^Z$ groups are each independently Cl, CF₃, NO₂, —S(O)₂N(R')₂ or an optionally substituted group selected from $C_{1-4}$ alkoxy, phenyl, phenyloxy, benzyl, or benzyloxy.

39. The compound according to claim 1, wherein R¹ is -(L)ₘAr¹, m is 0 or 1, Ar¹ is phenyl optionally substituted with 0-5 occurrences of $ZR^Y$, and compounds have one of the following formulas IIA or IIA-1:

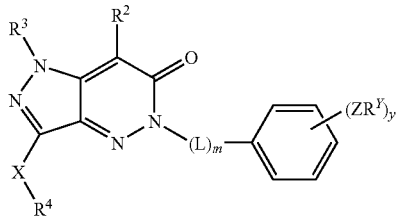

IIA

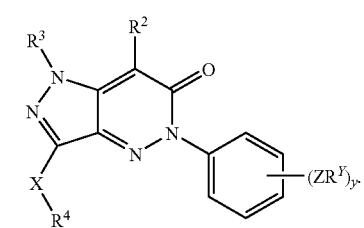

IIA-1

40. The compound according to claim 1, wherein R² is -(T)ₙR, wherein n is 0 and R is hydrogen, R¹ is -(L)ₘAr¹, wherein m is 0 or 1, Ar¹ is phenyl optionally substituted with 0-3 occurrences of $ZR^Y$, and compounds have one of the following formulas IIB or IIB-1:

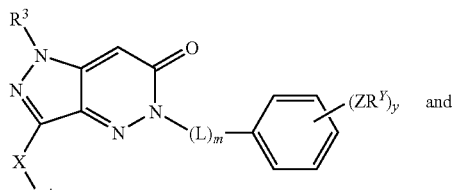

IIB

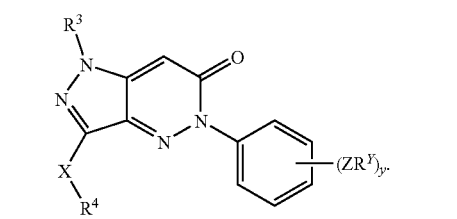

IIB-1

41. The compound according to claim 1, wherein R² is -(T)ₙR, wherein n is 0 and R is hydrogen, R³ is hydrogen, R¹ is -(L)ₘAr¹ wherein m is 0 or 1, Ar¹ is phenyl optionally substituted with 0-5 occurrences of $ZR^Y$, and compounds have one of the following formulas IIC or IIC-1:

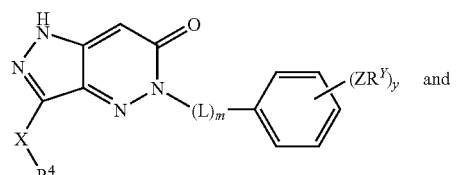

IIC

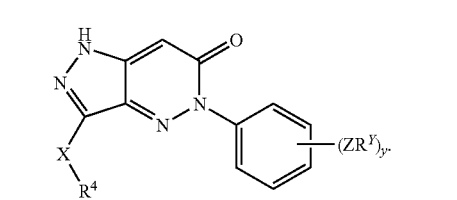

IIC-1

42. The compound according to claim 1, wherein R³ is hydrogen, R² is -(T)ₙR, wherein n is 0 and R is hydrogen, X is NR, R¹ is -(L)ₘAr¹ wherein m is 0 or 1, Ar¹ is phenyl optionally substituted with 0-5 occurrences of $ZR^Y$, and compounds have one of the following formulas IID or IID-1:

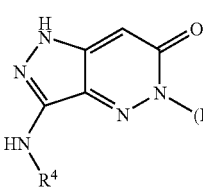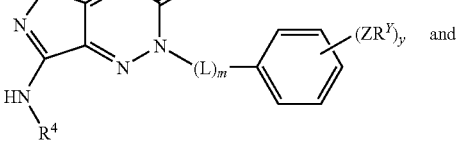

IID

IID-1

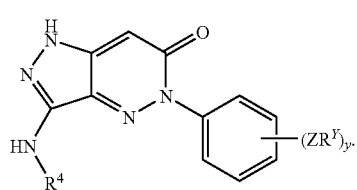

43. The compound according to claim 1, wherein R³ is hydrogen, R² is -(T)ₙR, wherein n is 0 and R is hydrogen, R¹ is -(L)ₘAr¹ wherein m is 0 or 1, Ar¹ is phenyl optionally substituted with 0-5 occurrences of ZR^Y, and compounds have one of the following formulas IIE, IIE-1, IIF, IIF-1, IIG, or IIG-1:

IIE

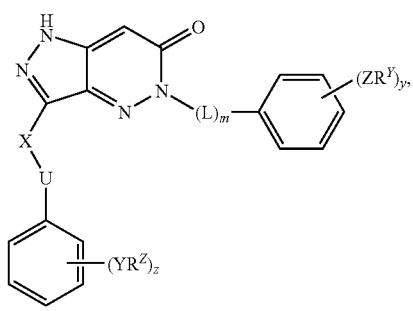

IIE-1

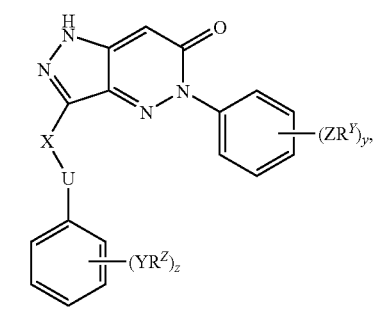

IIF

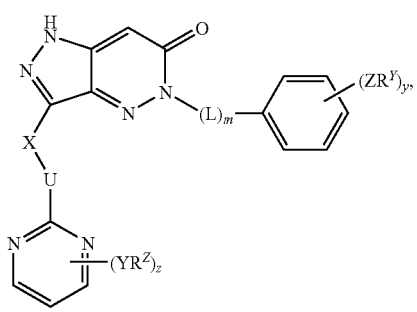

IIF-1

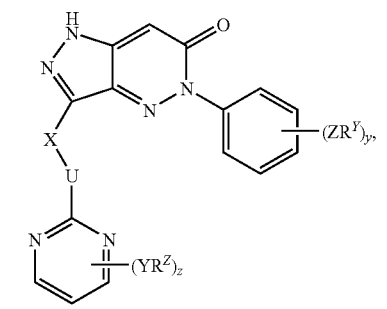

IIG

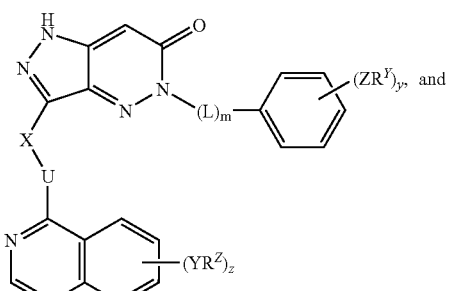

and

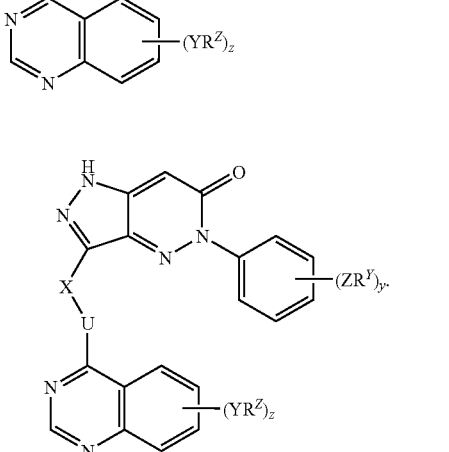

IIG-1

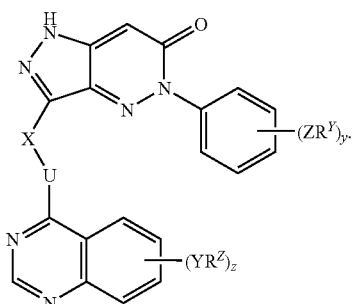

44. The compound according to claim 1, wherein R³ is hydrogen, R² is -(T)ₙR, wherein n is 0 and R is hydrogen, X is NH, R¹ is -(L)ₘAr¹ wherein m is 0 or 1, Ar¹ is phenyl optionally substituted with 0-5 occurrences of ZR^Y, and compounds have one of the following formulas IIIE, IIIE-1, IIIF, IIIF-1, IIIG, or IIIG-1:

IIIE

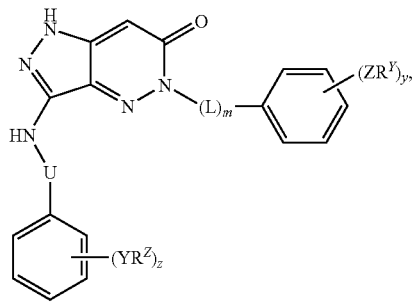

IIIE-1

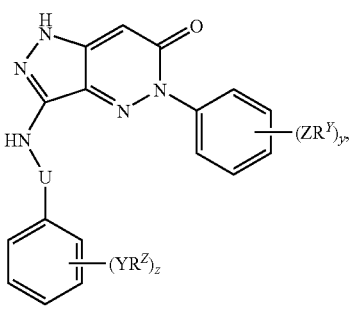

46. The compound according to claim 1, wherein $R^3$ and $R^4$ are hydrogen, wherein $R^2$ is -$(T)_nR$, wherein n is 0 and R is hydrogen, X is a valence bond, $Ar^1$ is optionally substituted phenyl, $R^1$ is -$(L)_mAr^1$, and compounds have one of the following formulas IIJ or IIJ-1:

47. The compound according to any one of claims 39-46, wherein $Ar^1$ is phenyl optionally substituted with 0-5 occurrences of $ZR^Y$ or wherein $Ar^1$ is pyridyl optionally substituted with 0-3 occurrences of $ZR^Y$.

48. The compound according to claim 47, wherein m is 0 or m is 1 and L is $CH_2$; y is 0-3; and each occurrence of $ZR^Y$ is independently halogen, $NO_2$, CN, or an optionally substituted group selected from $C_{1-4}$ aliphatic, aryl, aralkyl, —$N(R')_2$, —$CH_2N(R')_2$, —OR', —$CH_2OR'$, —SR', —$CH_2SR'$, —COOR', or —$S(O)_2N(R')_2$.

49. The compound according to claim 48, wherein each occurrence of $ZR^Y$ is independently Cl, $CF_3$, $NO_2$, —$S(O)_2N(R')_2$ or an optionally substituted group selected from $C_{1-4}$ alkoxy, phenyl, phenyloxy, benzyl, or benzyloxy.

50. The compound according to any one of claims 24-28, wherein $Ar^3$ is phenyl or quinazolyl optionally substituted with 0-5 occurrences of $YR^Z$ or wherein $Ar^3$ is pyridyl or pyrimidinyl optionally substituted with 0-3 occurrences of $YR^Z$.

51. The compound according to claim 50, wherein U is $CH_2$; X is NH; m is 0 or 1 and L is $CH_2$; y is 0-3; and each occurrence of $YR^Z$ are each independently halogen, $NO_2$, CN, or an optionally substituted group selected from $C_{1-4}$ alkyl, aryl, aralkyl, —$N(R')_2$, —$CH_2N(R')_2$, —OR', —$CH_2OR'$, —SR', —$CH_2SR'$, —COOR', or —$S(O)_2N(R')_2$.

52. The compound according to claim 1, selected from one of the following compounds:

45. The compound according to claim 1, wherein $R^3$ and $R^4$ are hydrogen, wherein $R^2$ is -$(T)_nR$, wherein n is 0 and R is hydrogen, X is NR, $Ar^1$ is optionally substituted phenyl, $R^1$ is -$(L)_mAr^1$, and compounds have one of the following formulas IIH or IIH-1:

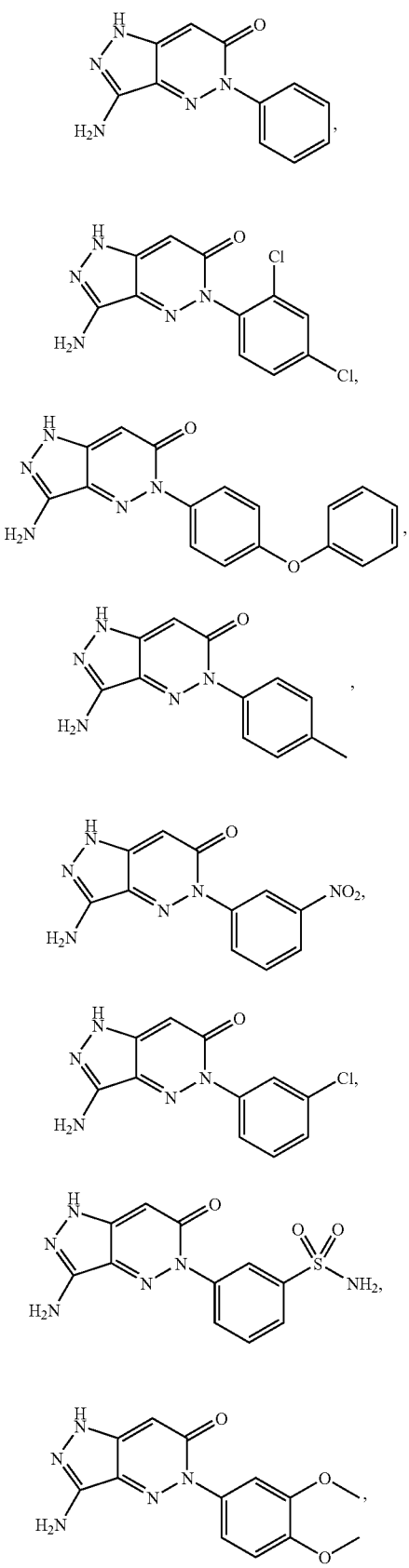

-continued
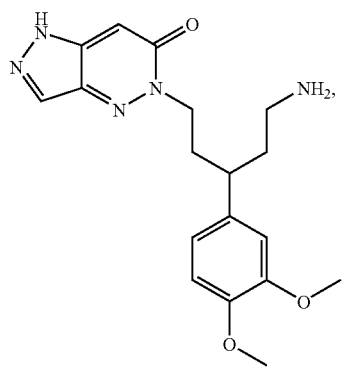
I-22
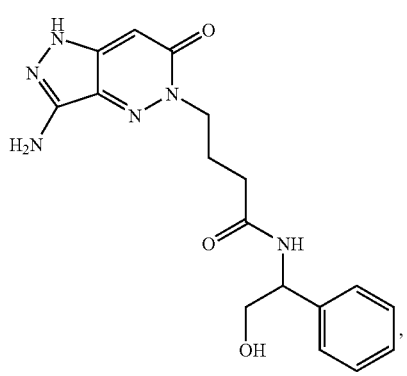
I-25
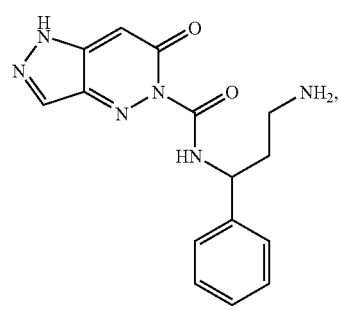
I-26
I-27
-continued
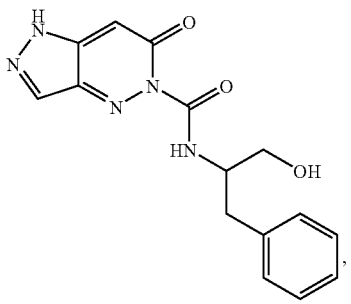
I-28
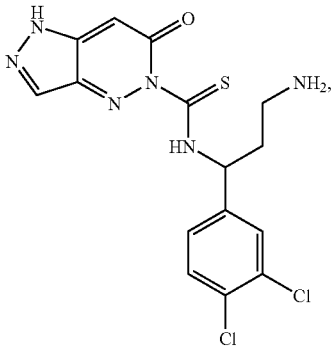
I-29
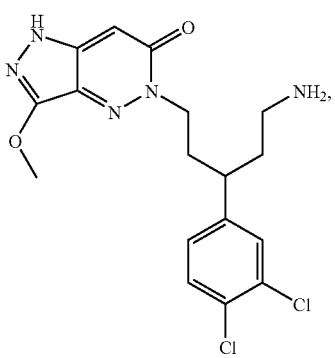
I-30
I-32

-continued
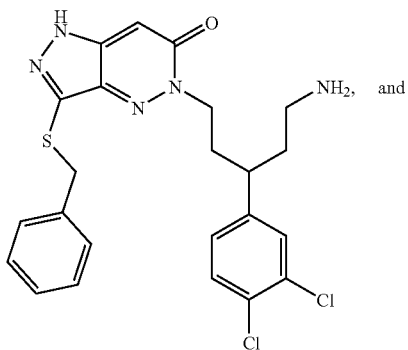
I-33
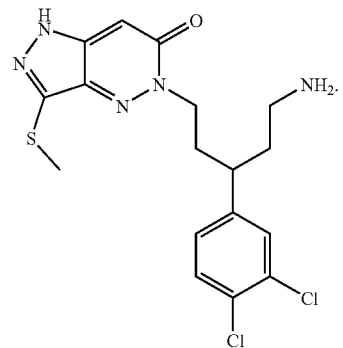
I-35
53. A pharmaceutically acceptable composition comprising a compound according to claim 1, and a pharmaceutically acceptable carrier, adjuvent, or vehicle.
* * * * *